(12) United States Patent
Aronhime et al.

(10) Patent No.: US 7,504,504 B2
(45) Date of Patent: Mar. 17, 2009

(54) METHODS OF PREPARING ARIPIPRAZOLE CRYSTALLINE FORMS

(75) Inventors: Judith Aronhime, Rehovot (IL); Ben-Zion Dolitzky, Petach-Tiqva (IL); Eran Luvchick, Azur (IL); Jean Hildesheim, Mazkeret Batya (IL); Hagit Eisen-Nevo, Petah-Tiqva (IL); Reuven Izsak, Doar Na Mizrah Binyamin (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 516 days.

(21) Appl. No.: 11/015,068

(22) Filed: Dec. 16, 2004

(65) Prior Publication Data

US 2005/0203299 A1  Sep. 15, 2005

Related U.S. Application Data

(60) Provisional application No. 60/530,297, filed on Dec. 16, 2003, provisional application No. 60/533,831, filed on Dec. 30, 2003, provisional application No. 60/618,404, filed on Oct. 13, 2004, provisional application No. 60/618,960, filed on Oct. 14, 2004.

(51) Int. Cl.
*C07D 401/12* (2006.01)
(52) U.S. Cl. ..................................... 544/363
(58) Field of Classification Search ................. 544/363
See application file for complete search history.

(56) References Cited

U.S. PATENT DOCUMENTS

| 4,734,416 | A | 3/1988 | Banno et al. |
| 5,006,528 | A | 4/1991 | Oshiro et al. |
| 5,314,506 | A | 5/1994 | Midler, Jr. et al. |
| 6,221,153 | B1 | 4/2001 | Castor et al. |
| 2003/0176703 | A1 | 9/2003 | Mendelovici et al. |
| 2004/0192915 | A1 | 9/2004 | Tsujimori et al. |
| 2005/0058935 | A1 | 3/2005 | Kishimura et al. |
| 2005/0152981 | A1 | 7/2005 | Gleeson et al. |
| 2005/0159429 | A1 | 7/2005 | Parthasaradhi et al. |
| 2005/0234071 | A1 | 10/2005 | Parthasaradhi et al. |
| 2005/0277650 | A1 | 12/2005 | Venkataraman et al. |
| 2006/0079690 | A1 | 4/2006 | Naddaka et al. |

FOREIGN PATENT DOCUMENTS

| JP | 02191256 | 7/1990 |
| WO | WO 03/026659 | 4/2003 |
| WO | WO 03/102009 | 12/2003 |
| WO | WO 2004/083183 A | 9/2004 |
| WO | WO 2004/099152 | 11/2004 |
| WO | WO 2004/106322 A | 12/2004 |
| WO | WO 2005/009990 A1 | 2/2005 |
| WO | WO 2006/012237 | 2/2006 |
| WO | WO 2006/030446 | 3/2006 |

OTHER PUBLICATIONS

Aoki, et al. "Study on Crystal Transformation of Aripiprazol", *The Fourth Japan-Korea Symposium On Separation Technology*, 1996, 937-940.
Oshiro Yasuo, et al. "Novel Antipsychotic Agents with Dopamine Autoreceptor Agonist Properties: Synthesis and Pharmacology of 7-'4-(4-Phenyl-1-piperaziny 1) butoxy-3,4-dihydro-2(1H)-quinolinone Derivatives", J. of Med. Chem., vol. 41, 1998, 658-667.
Oshiro et al., "Novel Antipsychotic Agents with Dopamine Autoreceptor Agonist Properties: Synthesis and Pharmacology of 7-[4-(4-Phenyl-1-piperazinyl)butoxyl]-3,4-dihydro-2(1H)-quinolinone Derivatives", *J. Med. Chem.*, 1998, 41, 658-667.

*Primary Examiner*—James O Wilson
*Assistant Examiner*—Ebenezer Sackey
(74) *Attorney, Agent, or Firm*—Kenyon & Kenyon LLP

(57) ABSTRACT

The invention encompasses aripiprazole crystalline forms, methods of preparing the same, and pharmaceutical compositions having aripiprazole crystalline forms.

11 Claims, 24 Drawing Sheets

METHODS OF PREPARING ARIPIPRAZOLE CRYSTALLINE FORMS

RELATED APPLICATIONS

This application claims the benefit of U.S. provisional Application No. 60/530,297, filed Dec. 16, 2003; U.S. provisional Application No. 60/533,831, filed Dec. 30, 2003; U.S. provisional Application No. 60/618,404, filed Oct. 13, 2004; and U.S. provisional Application No. 60/618,960, filed Oct. 14, 2004.

FIELD OF THE INVENTION

The invention encompasses crystalline forms of aripiprazole forms and methods of preparing them.

BACKGROUND OF THE INVENTION

Schizophrenia is the most common type of psychosis caused by excessive neurotransmission activity of the dopaminergic nervous system in the central nervous system. A number of drugs which block the neurotransmission of dopaminergic receptor in the central nervous system have been developed for use in treating schizophrenia. Among the drugs developed are phenothiazine-type compounds such as chlorpromazine, butyrophenone-type compounds such as haloperidol, and benzamide-type compounds such as sulpiride. These drugs improve so-called positive symptoms in the acute period of schizophrenia such as hallucinations, delusions, and excitations. Many drugs for treating schizophrenia, however, are not effective for improving the so-called negative symptoms which are observed in the chronic period of schizophrenia such as apathy, emotional depression, and hypopsychosis. The drugs currently used produce undesirable side effects such as akathisia, dystonia, Parkinsonism dyskinesia, and late dyskinesia, by blocking the neurotransmission of dopaminergic receptor in the striate body. Drugs that improve both the negative and positive symptoms of schizophrenia but diminish the undesirable side effect of schizophrenia are particularly desirable.

Aripiprazole is a pyschotropic drug that exhibits high affinity for dopamine $D_2$ and $D_3$, serotonin $5\text{-}HT_{1A}$ and $5\text{-}HT_{2A}$ receptors; moderate affinity for dopamine $D_4$, serotonin $5\text{-}HT_{2C}$ and $5\text{-}HT_7$, $\alpha_1$-adrenergic and histamine $H_1$ receptors; and moderate affinity for the serotonin reuptake site. Aripiprazole has no appreciable affinity for cholinergic muscarinic receptors. The mechanism of action of aripiprazole, as with other drugs having efficacy in schizophrenia, is unknown. It has been proposed, however, that the efficacy of aripiprazole is mediated through a combination of partial agonist activity at $D_2$ and $5\text{-}HT_{1A}$ receptors and antagonist activity at $5\text{-}HT_{2A}$ receptors.

Japanese Patent Kokai No. 02-191256 discloses that anhydride crystals of aripiprazole are typically manufactured by recrystallization of anhydride aripiprazole from ethanol or by heating aripiprazole hydrate at a temperature of 80° C. According to WO 03/26659, anhydride aripiprazole prepared by these methods is significantly hygroscopic.

The Proceedings of the 4th Japanese-Korean Symposium on Separation Technology (Oct. 6-8, 1996) disclosed that aripiprazole anhydride crystals may exist as Type-I and Type-II crystals. Type-I aripiprazole crystals can be prepared by recrystallizing aripiprazole from an ethanol solution or by heating aripiprazole hydrate at 80° C. Type-II aripiprazole crystals can be prepared by heating the Type-I crystals at 130° C. to 140° C. for 15 hours. This process is not easily applied to an industrial scale preparation of anhydride aripiprazole.

PCT publication WO 03/26659 discloses the preparation of anhydrous aripiprazole Type I and crystalline forms Form A, B, C, and D. Typically, the process for preparing the crystalline forms comprises heating crystalline anhydrous aripiprazole. The process, however, is cumbersome because it requires crystalline anhydrous aripiprazole as the starting material. The process in the PCT publication can only be carried out after the preparation, isolation, and purification of aripiprazole. Thus, only after performing the additional steps may one heat the crystalline anhydrous aripiprazole to obtain the desired crystalline forms of aripiprazole. Additionally, drying or heating may affect the distribution of crystalline forms and/or crystalline purity, if drying causes crystalline transformation from one crystalline form to another.

Alternate crystalline structures possessing the stability and manufacturing advantages of anhydrous aripiprazole are highly desired. Likewise, methods for making aripiprazole without additional steps and cost also are necessary.

SUMMARY OF THE INVENTION

The invention encompasses anhydrous aripiprazole crystalline forms which are non-hygroscopic and which maintain compound stability during storage, and methods for preparing the non-hygroscopic aripiprazole crystalline forms.

One embodiment of the invention encompasses a crystalline anhydrous aripiprazole Form I characterized by X-ray powder diffraction peaks at 16.8, 19.6, 20.6, 22.3, and 25.1 degrees two-theta, ±0.2 degrees two-theta.

Another embodiment of the invention encompasses aripiprazole Form II characterized by X-ray powder diffraction peaks at 16.5, 18.7, 21.9, 22.4, and 23.5 degrees two-theta, ±0.2 degrees two-theta.

Another embodiment of the invention encompasses substantially pure crystalline aripiprazole Form II. For example, substantially pure Form II may encompass Form II having less than 40% by weight of other crystalline aripiprazole forms and preferably no more than 10% by weight of other crystalline aripiprazole forms.

Particular embodiments of the invention encompass Form II having no more than 40% by weight of crystalline compound 1, crystalline compound 2, Form C, or Form D. In another embodiment, Form II has no more than 30% by weight of crystalline compound 1, crystalline compound 2, Form C, or Form D, preferably no more than 20%, more preferably no more than 10%, and most preferably no more than 5% by weight.

Another embodiment of the invention encompasses crystalline aripiprazole Form VI characterized by X-ray powder diffraction peaks at 17.6, 17.8, 20.6, and 24.9 degrees two-theta, ±0.2 degrees two-theta.

Yet another embodiment of the invention encompasses aripiprazole crystalline Form VIII characterized by X-ray powder diffraction peaks at 4.4, 8.7, 20.8, 21.6, and 26.0 degrees two-theta, ±0.2 degrees two-theta. Another embodiment of the invention encompasses crystalline aripiprazole Form X characterized by X-ray powder diffraction peaks at 18.2, 22.4, 22.8, and 24.3 degrees two-theta, ±0.2 degrees two-theta.

Yet another embodiment of the invention encompasses aripiprazole crystalline Form XI characterized by X-ray powder diffraction peaks at 5.9, 18.0, 20.5, 24.5, and 25.1 degrees two-theta, ±0.2 degrees two-theta.

Another embodiment of the invention encompasses crystalline aripiprazole Form XIV characterized by X-ray powder diffraction peaks at 11.0, 23.6, 24.7, 25.2, and 29.0 degrees two-theta, ±0.2 degrees two-theta.

Another embodiment of the invention encompasses crystalline aripiprazole Form XIX characterized by X-ray powder diffraction peaks at 17.4, 18.7, 20.0, 23.3, and 24.5 degrees two-theta, ±0.2 degrees two-theta.

Another embodiment of the invention encompasses crystalline aripiprazole Form XX characterized by X-ray powder diffraction peaks at 19.6, 20.4, 20.8, 22. 1, and 24.5 degrees two-theta, ±0.2 degrees two-theta.

Another embodiment of the invention encompasses a method of preparing Form II by slurrying crystalline aripiprazole compound 2 in acetone at room temperature to form Form II, and collecting the Form II.

Yet another embodiment of the invention encompasses methods for preparing crystalline aripiprazole comprising dissolving aripiprazole in a solvent to form a mixture, heating the mixture from about 40° C. to about 132° C., cooling the mixture to form a aripiprazole precipitate, and collecting the precipitate.

A second method of preparing crystalline aripiprazole comprises dissolving aripiprazole in a solvent to form a mixture, heating the mixture to the solvent's boiling point until aripiprazole dissolves, adding a co-solvent to precipitate aripiprazole, cooling the mixture to about room temperature to about 4° C., and collecting the precipitate. The second method may further comprise cooling the aripiprazole solvent mixture to the boiling point of the co-solvent before adding the co-solvent if the boiling point of the co-solvent is lower than the boiling point of the solvent.

One embodiment of the invention encompasses methods of preparing Form I comprising providing aripiprazole crystalline Form X and drying Form X to obtain Form I.

Another embodiment of the invention encompasses methods of preparing crystalline Form II comprising providing aripiprazole crystalline compound 1 and drying compound 1 to obtain Form II.

Yet another embodiment of the invention encompasses methods of preparing crystalline Compound 2 comprising providing at least one of aripiprazole Form D, Form X, Form XI, Form XII, or Form XIX, and heating the aripiprazole to obtain Compound 2.

Yet another embodiment of the invention encompasses methods of preparing crystalline Compound 2 comprising providing Form X, and drying the aripiprazole to obtain Compound 2.

Another embodiment of the invention encompasses methods of preparing crystalline Form C comprising providing Form II, crystalline Compound 1, or crystalline Compound 2, and heating aripiprazole to obtain Form C.

Yet another embodiment encompasses methods of preparing Form D comprising providing aripiprazole crystalline Compound 1, crystalline Compound 2, or Form XIV, and drying the aripiprazole to obtain Form D.

Another embodiment of the invention encompasses methods of preparing a mixture of crystalline Compound 2 and Compound 1 comprising providing aripiprazole Form XI and drying Form XI to obtain a mixture of aripiprazole crystalline Compound 2 and crystalline Compound 1.

Yet another embodiment of the invention encompasses methods of preparing a mixture of Form D, Compound 1, and crystalline Compound 2 comprising providing a mixture of Form D and Compound 1, and drying the mixture to obtain a mixture of Form D, Compound 1, and crystalline Compound 2.

Other embodiments of the invention encompass pharmaceutical compositions comprising aripiprazole crystalline forms of the invention and methods of treating schizophrenia using these pharmaceutical compositions.

DETAILED DESCRIPTION OF THE INVENTION

The time and expense required to prepare aripiprazole on an industrial scale is decreased by using the anhydrous aripiprazole crystals of the invention. Specifically, the anhydrous aripiprazole forms of the invention diminish the adherence of aripiprazole to equipment during industrial preparation, which in turn diminishes the necessity of special handling techniques to maintain the equipment and anhydrous aripiprazole. The invention also encompasses aripiprazole crystalline forms that can be prepared directly by slurrying, rather than by heating a preexisting hydrate crystal form, thereby eliminating unnecessary process steps during manufacture. The invention also encompasses methods of preparing crystalline Compound 2 by crystallization and shorter drying processes than the drying process for aripiprazole crystalline forms disclosed in WO 03/26659.

The aripiprazole forms encompassed by the invention may be characterized by at least one of Karl Fisher or TGA, X-Ray power diffraction (XRD), or differential scan calorimetry (DSC).

As used herein, the tern "anhydrous" refers to aripiprazole crystal forms with less than about 0.5% moisture.

Figure 1:
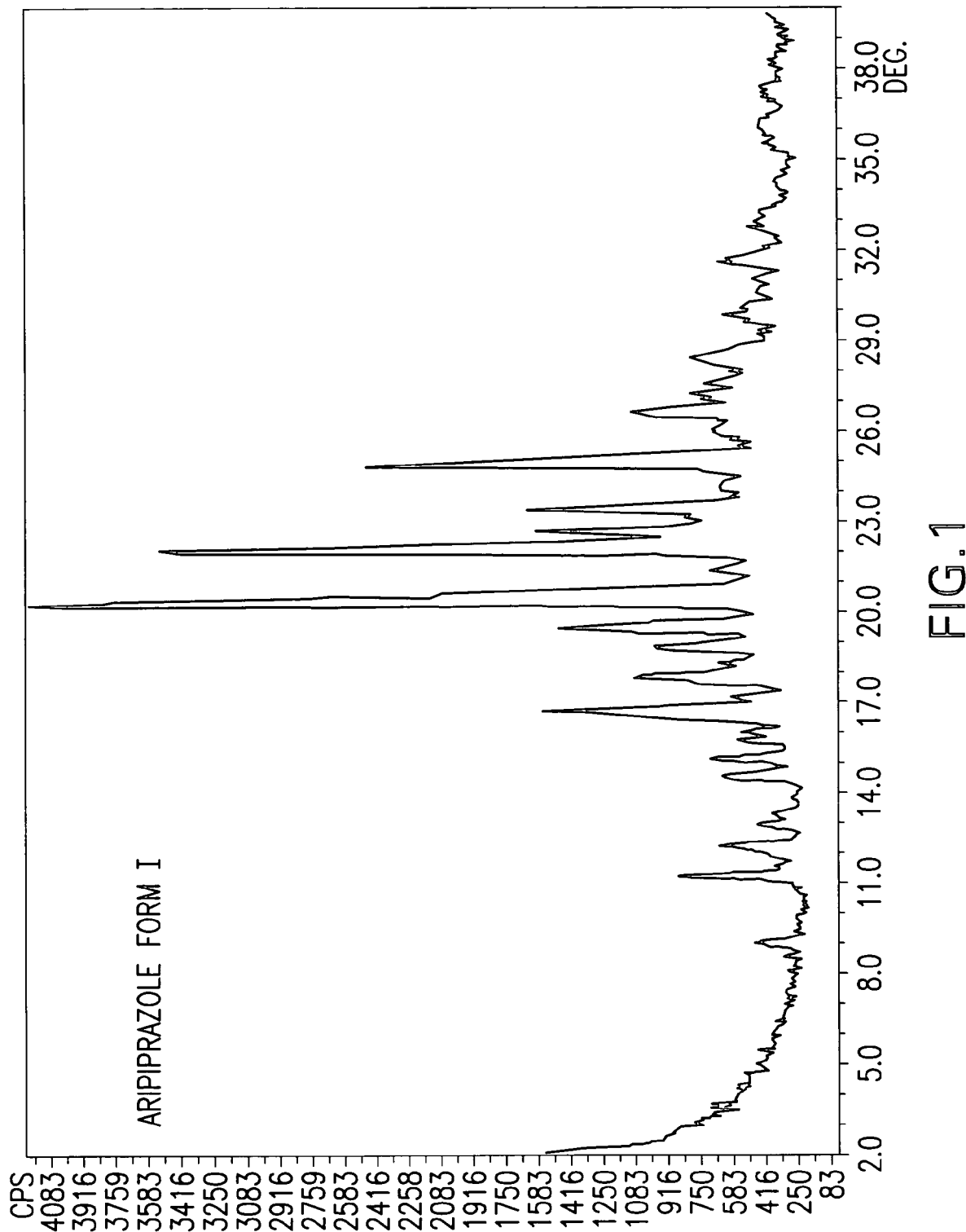
FIG. 1 illustrates the powder X-ray diffraction pattern for Form I.
Figure 11:
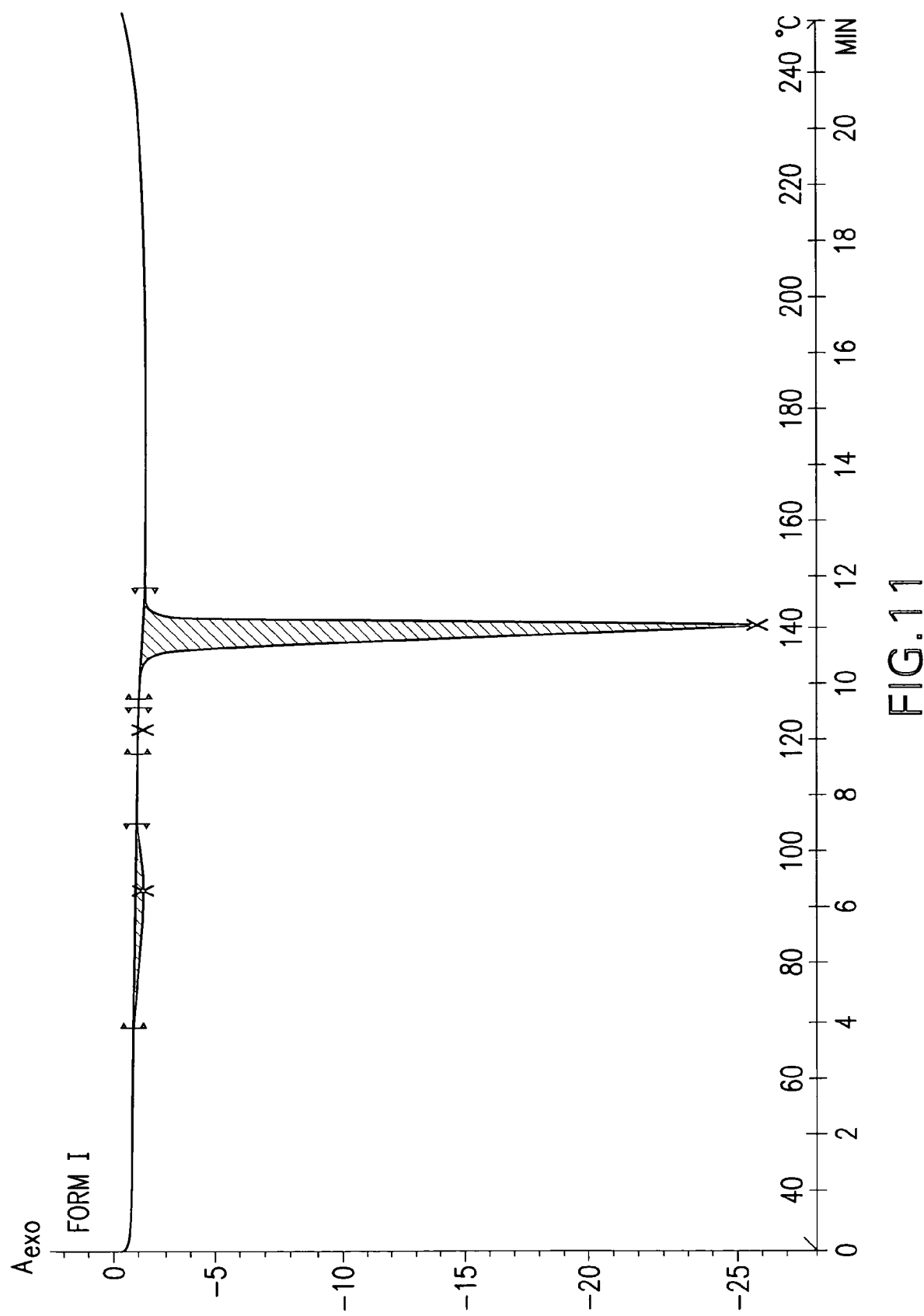
FIG. 11 illustrates the differential scan calorimetry analysis for Form I.

One embodiment of the invention encompasses a crystalline anhydrous aripiprazole form, herein defined as Form I, having about 0.7% moisture by weight as measured by Karl Fisher or TGA. Form I may be characterized by X-ray powder diffraction peaks at 16.8, 19.6, 20.6, 22.3, and 25.1 degrees two-theta, ±0.2 degrees two-theta. Form I may be characterized further by X-ray powder diffraction peaks at 11.3, 12.3, 14.6, 15.2, 17.9, 22.8, and 23.6 degrees two-theta, ±0.2 degrees two-theta. Form I may be characterized also by a melting endotherm at about 139° C. to about 140° C. (about 90 J/g melting enthalpy) as measured by differential scanning calorimetry (DSC). Form I may be substantially identified by either the XRD pattern of FIG. 1 or the DSC of FIG. 11.

Figure 2:
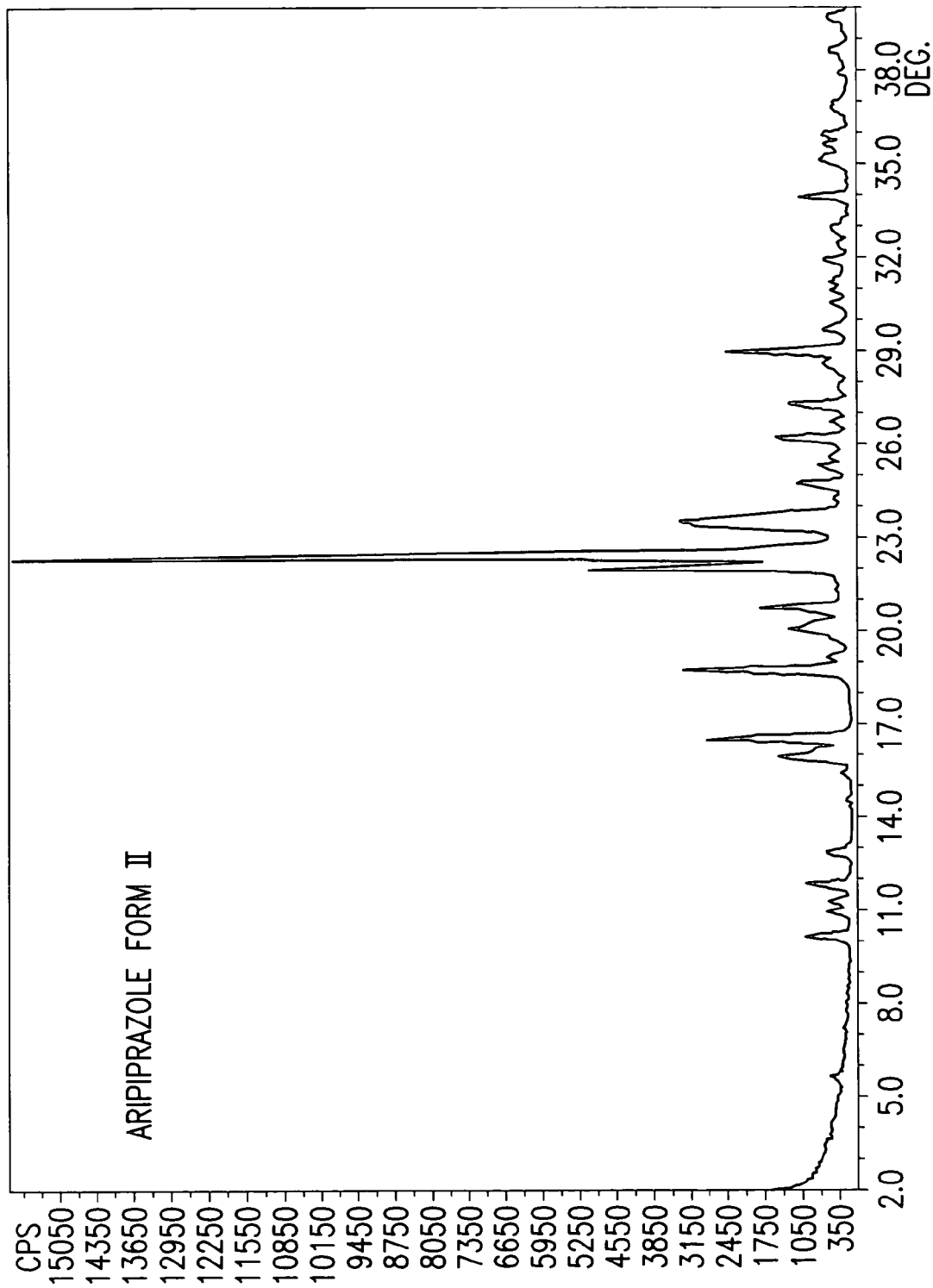
FIG. 2 illustrates the powder X-ray diffraction pattern for Form II.
Figure 12:
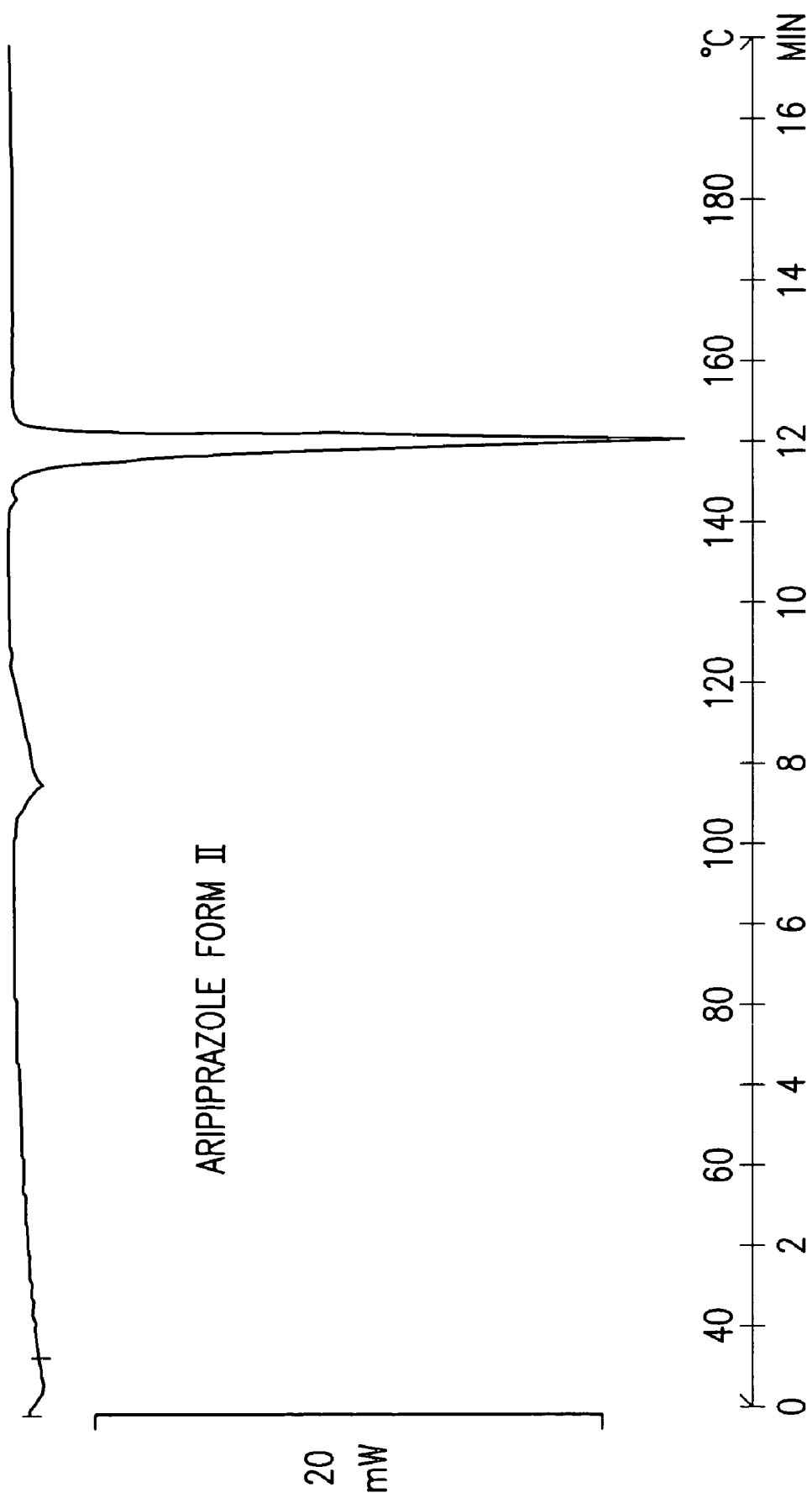
FIG. 12 illustrates the differential scan calorimetry analysis for Form II.

Another embodiment of the invention is a crystalline aripiprazole form, herein defined as Form II, having about 0.3% moisture by weight as measured by Karl Fisher or TGA. Form II may be characterized by X-ray powder diffraction peaks at 16.5, 18.7, 21.9, 22.4, and 23.5 degrees two-theta, ±0.2 degrees two-theta. Form II may be characterized further by X-ray powder diffraction peaks at 10.2, 11.8, 20.0, 20.7, 26.2, 27.3, and 29.0 degrees two-theta, ±0.2 degrees two-theta. Form II may be characterized also by DSC showing a broad and small endotherm in the range of about 100° C. to about 130° C. and a melting endotherm at about 148° C. to about 150° C. The latter indicating a transformation to Form C. Form II may be substantially identified by either the XRD pattern of FIG. 2 or the DSC of FIG. 12.

Another embodiment of the invention encompasses substantially pure Form II. As used herein, the term "substantially pure" refers to Form II having less than 40% of other aripiprazole crystalline forms and more preferably no more than 10% by weight of other aripiprazole crystalline forms.

A particular embodiment of the invention encompasses Form II having no more than 40% by weight of crystalline Compound 1, crystalline Compound 2, Form C, or Form D. In another particular embodiment, Form II has no more than 30% by weight of crystalline Compound 1, crystalline Compound 2, Form C, or Form D, preferably no more than 20%, more preferably no more than 10%, and most preferably no more than 5% by weight.

As used herein, "crystalline compound 1" refers to an aripiprazole crystalline form characterized by X-ray powder diffraction peaks at 15.5, 19.5, 22.6, 24.9, and 30.6 degrees two-theta, 0.2 degrees two-theta. As used herein, "crystalline compound 2" refers to an aripiprazole crystalline form characterized by X-ray powder diffraction peaks at 8.8, 14.5, 17.8, 20.5, and 22.2 degrees two-theta, 0.2 degrees two-theta.

Figure 20:
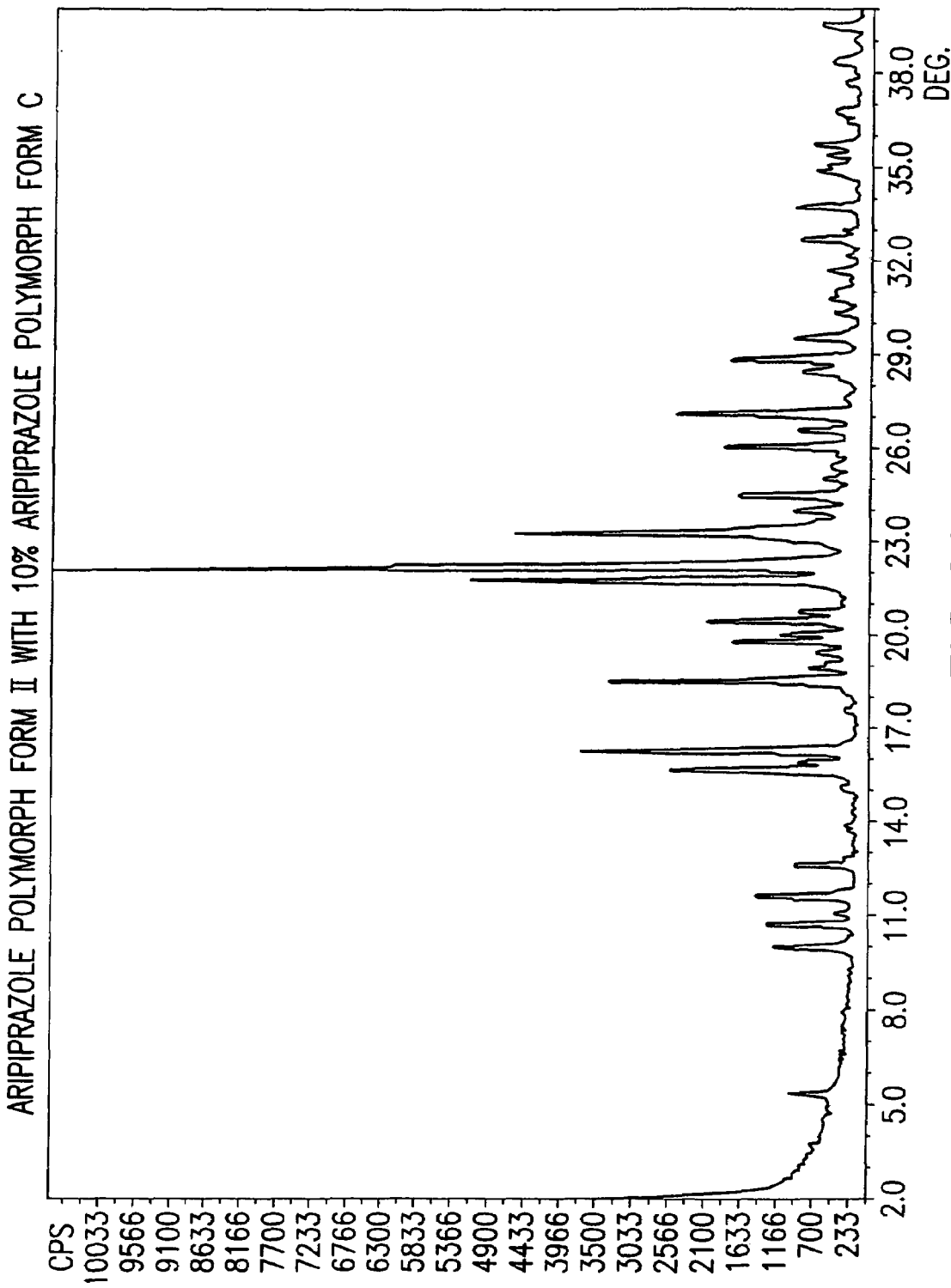
FIG. 20 illustrates the powder X-ray diffraction pattern for Form II having 10% of Form C.
Figure 21:
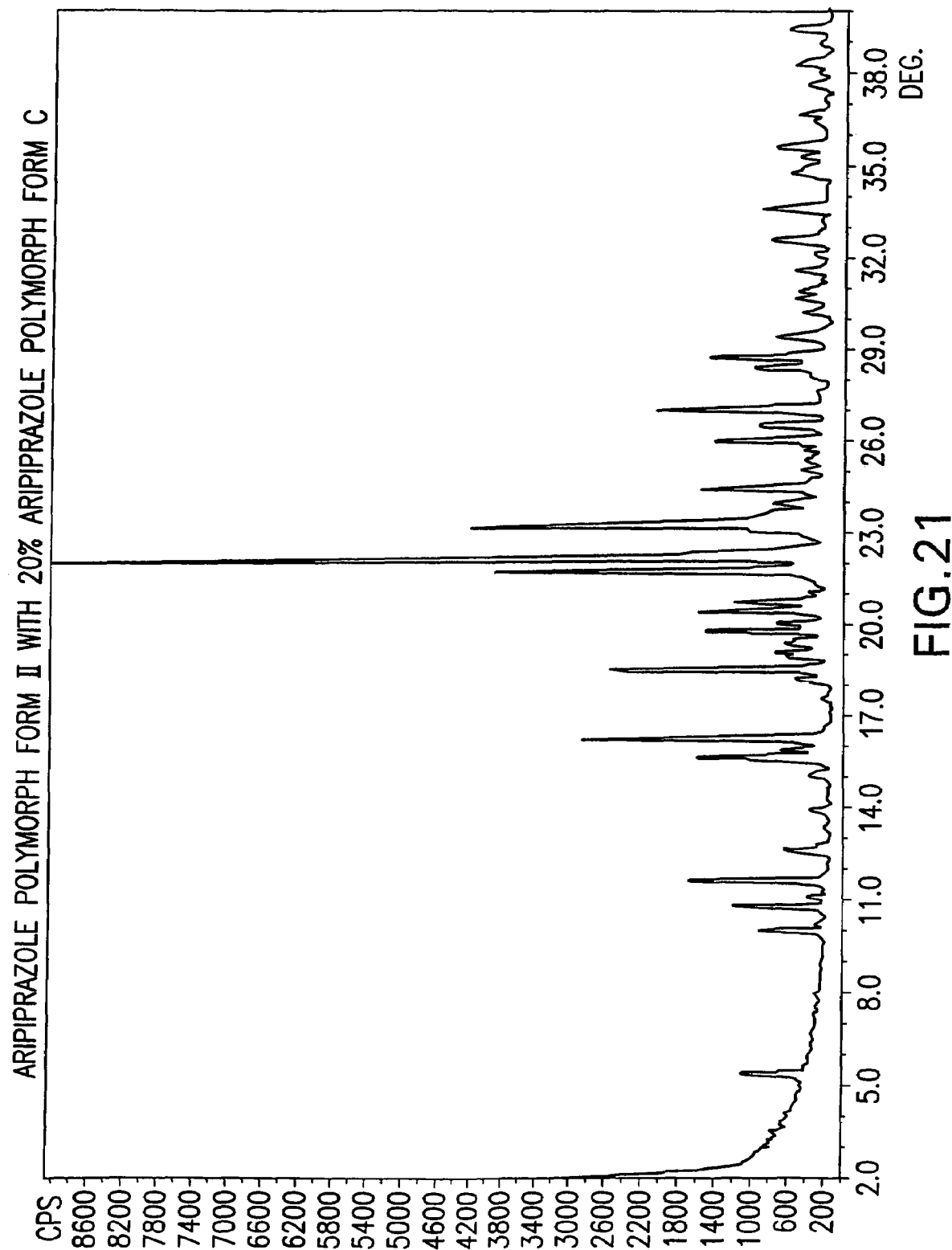
FIG. 21 illustrates the powder X-ray diffraction pattern for Form II having 20% of Form C.
Figure 22:
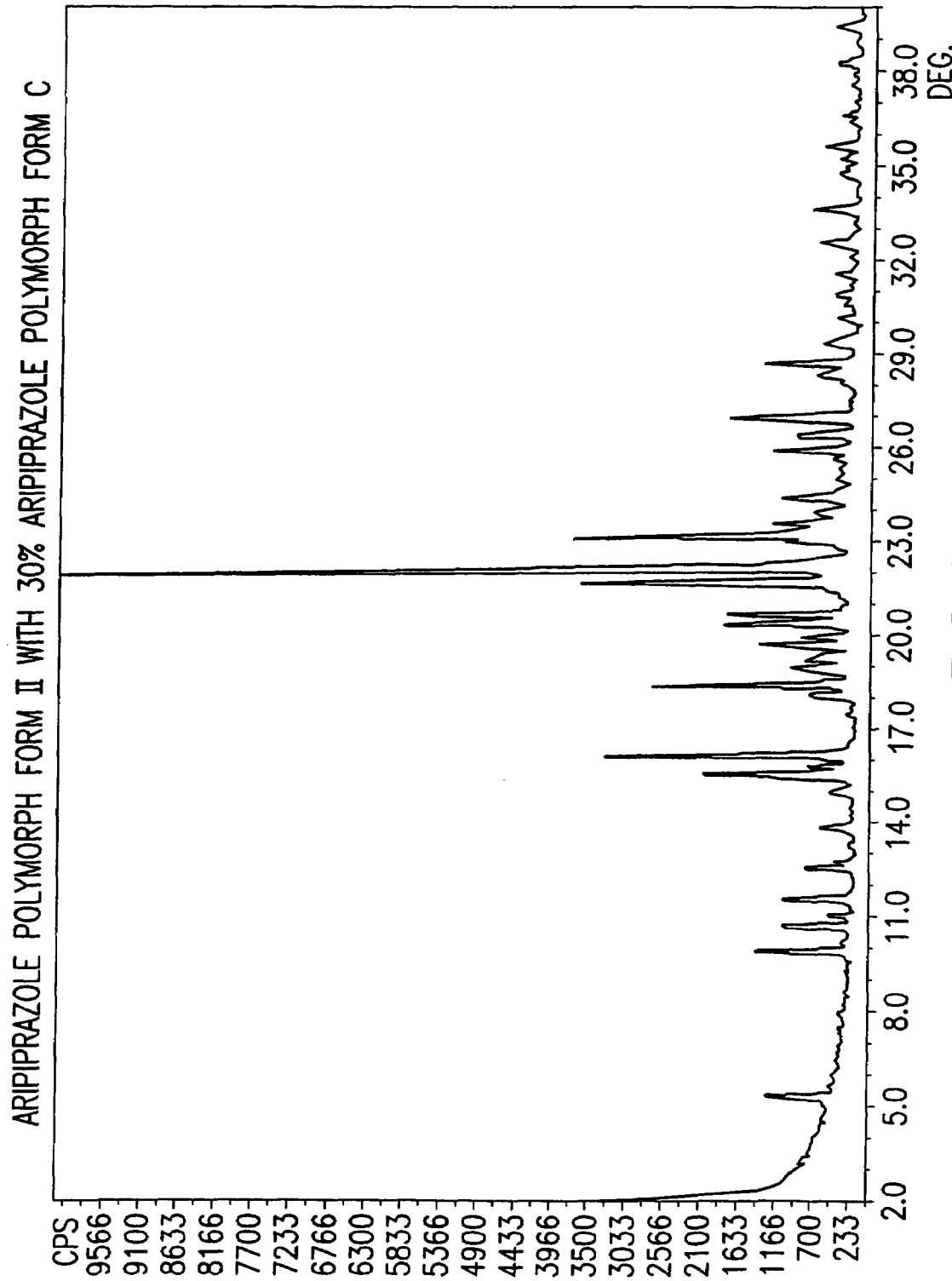
FIG. 22 illustrates the powder X-ray diffraction pattern for Form II having 30% of Form C.
Figure 23:
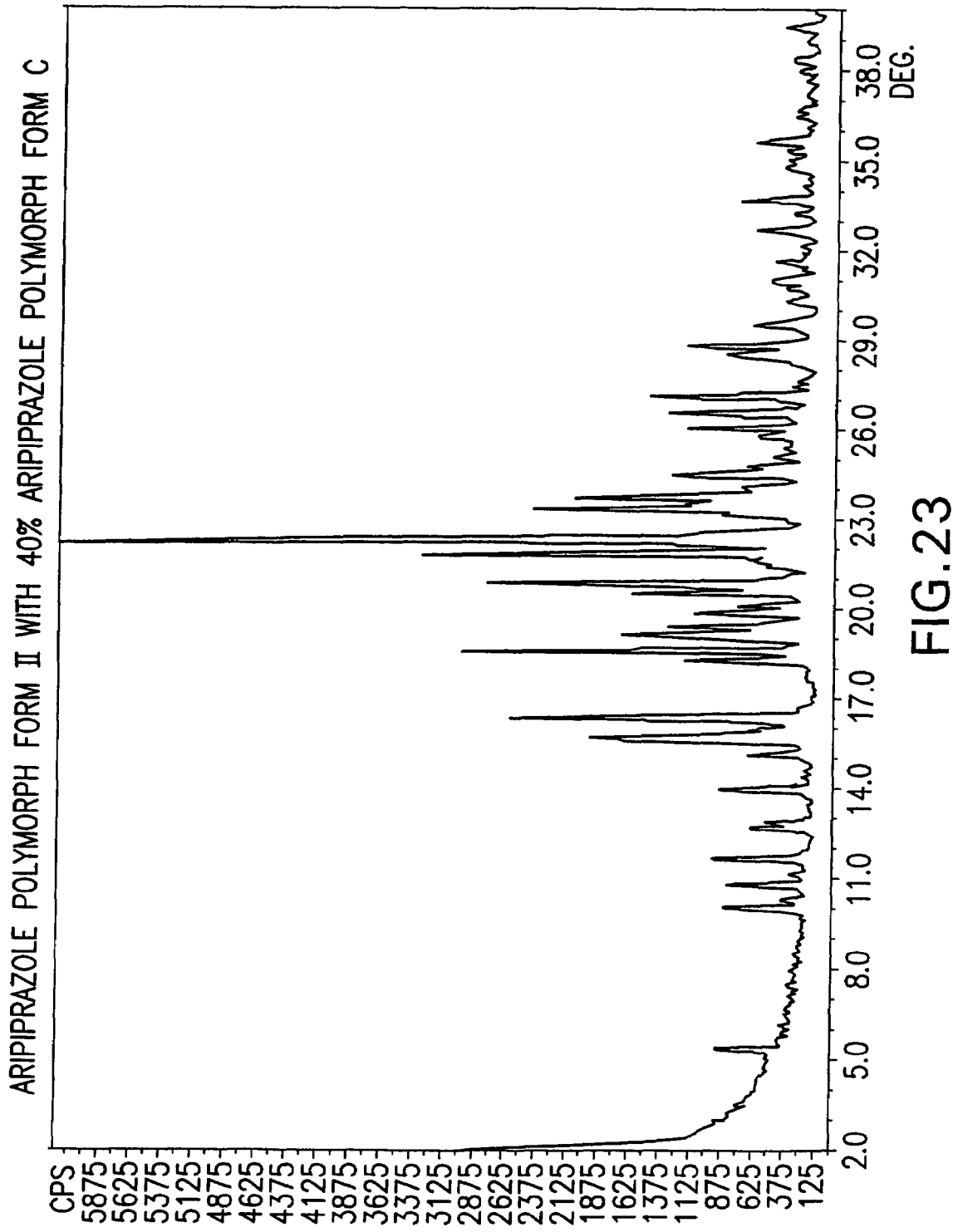
FIG. 23 illustrates the powder X-ray diffraction pattern for Form II having 40% of Form C.
Figure 24:
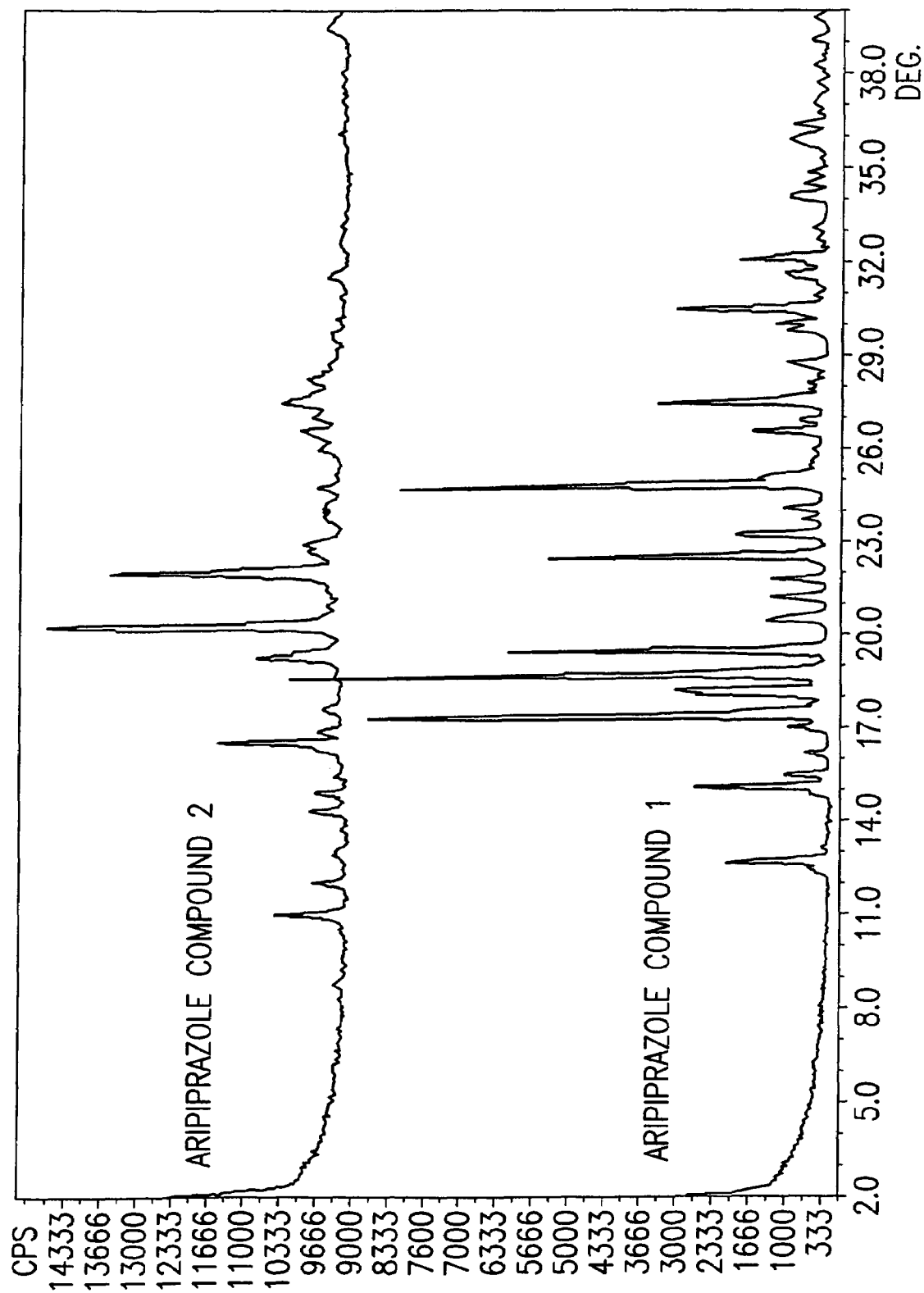
FIG. 24 is a staggered figure illustrating the X-ray diffraction patterns for crystalline Compound 1 and crystalline Compound 2.

FIG. 20 illustrates an X-ray diffraction pattern of Form II having 10% Form C by weight. FIG. 21 illustrates an X-ray diffraction pattern of Form II having 20% Form C by weight. FIG. 22 illustrates an X-ray diffraction pattern of Form II having 30% Form C by weight. FIG. 23 illustrates an X-ray diffraction pattern Form II having 40% Form C by weight.

Figure 3:
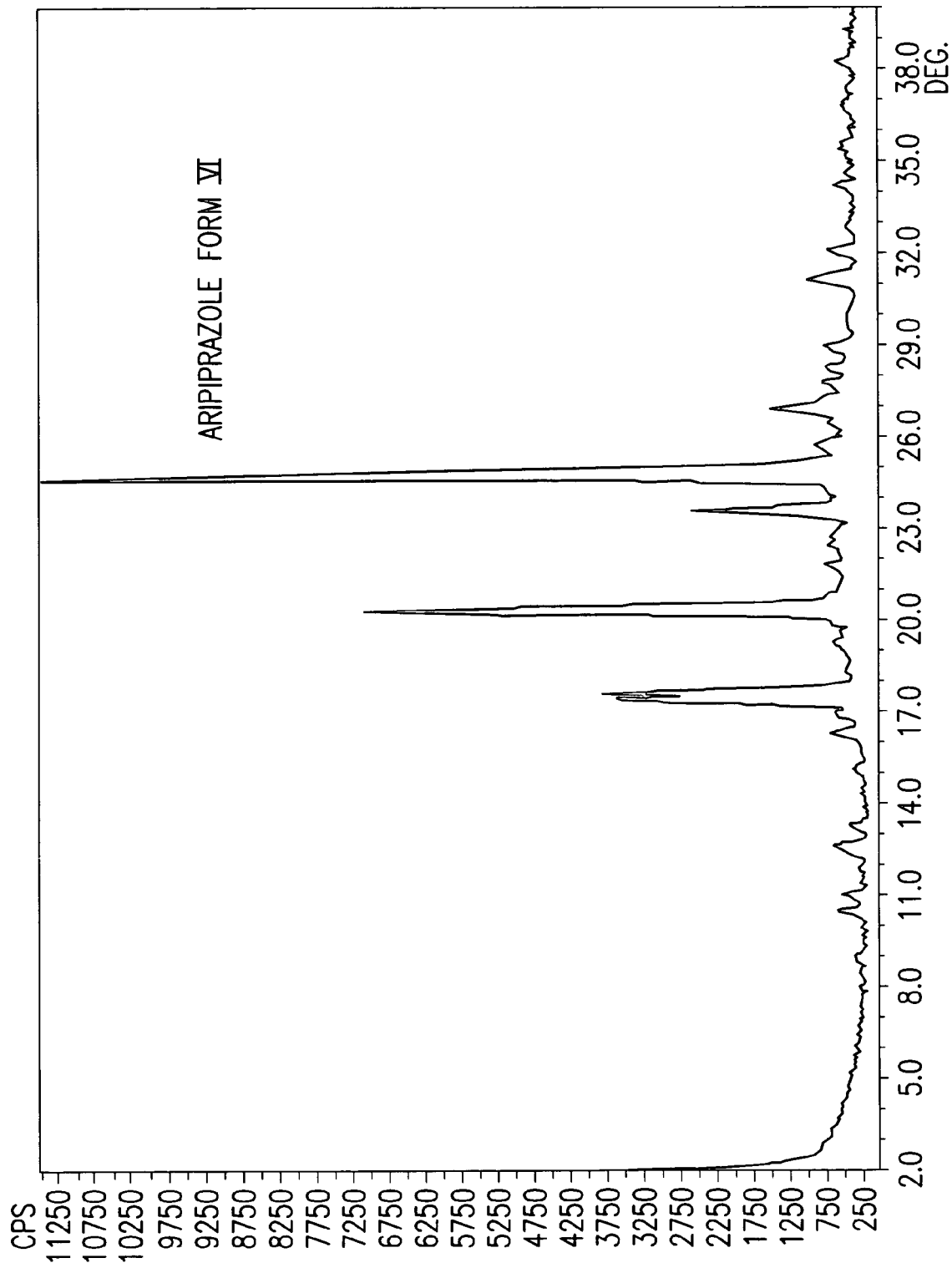
FIG. 3 illustrates the powder X-ray diffraction pattern for Form VI.
Figure 13:
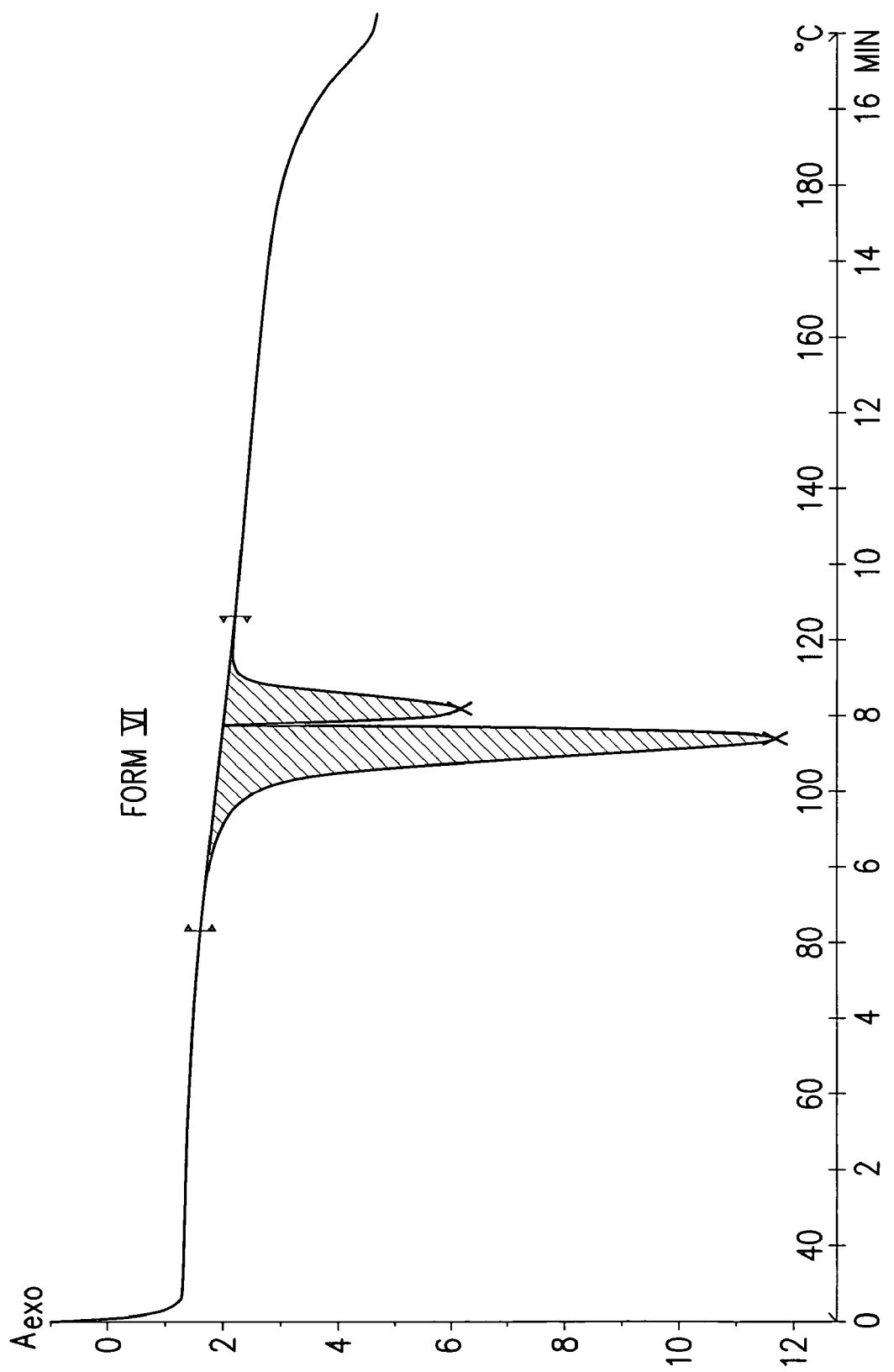
FIG. 13 illustrates the differential scan calorimetry analysis for Form VI.

Another embodiment of the invention encompasses is a crystalline aripiprazole form, herein defined as Form VI, having about 0.2% moisture by weight as measured by TGA. Form VI may be characterized by X-ray powder diffraction peaks at 17.6, 17.8, 20.6, and 24.9 degrees two-theta, ±0.2 degrees two-theta. Form VI may be characterized further by X-ray powder diffraction peaks at 23.7, 27.0, and 31.2 degrees two-theta, ±0.2 degrees two-theta. The typical DSC of Form VI shows two endotherm peaks, a first peak at about 105° C., and a second peak at about 110° C. Aripiprazole Form VI may be substantially identified by either the XRD pattern of FIG. 3 or the DSC of FIG. 13.

Figure 4:
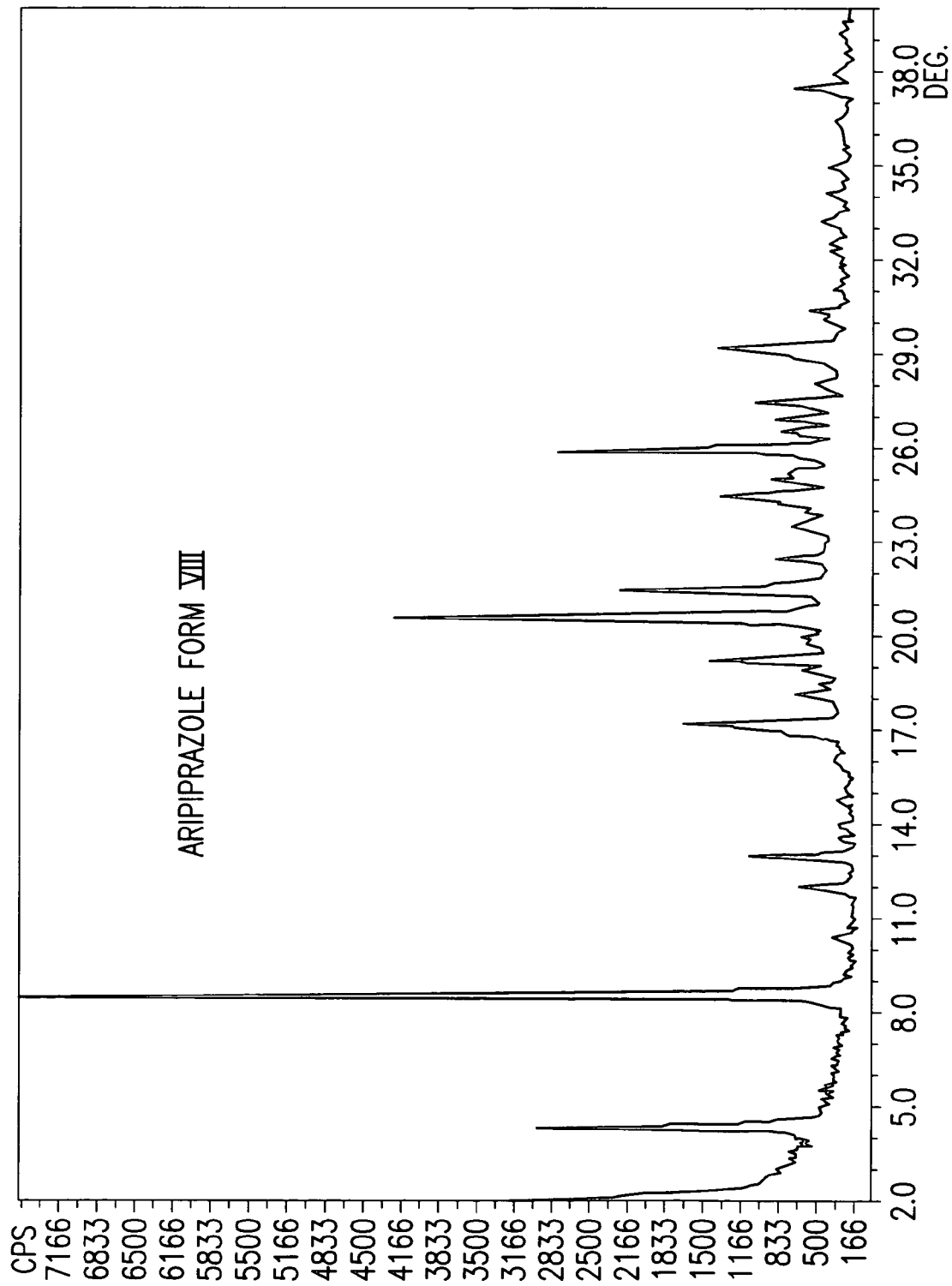
FIG. 4 illustrates the powder X-ray diffraction pattern for Form VIII.
Figure 14:
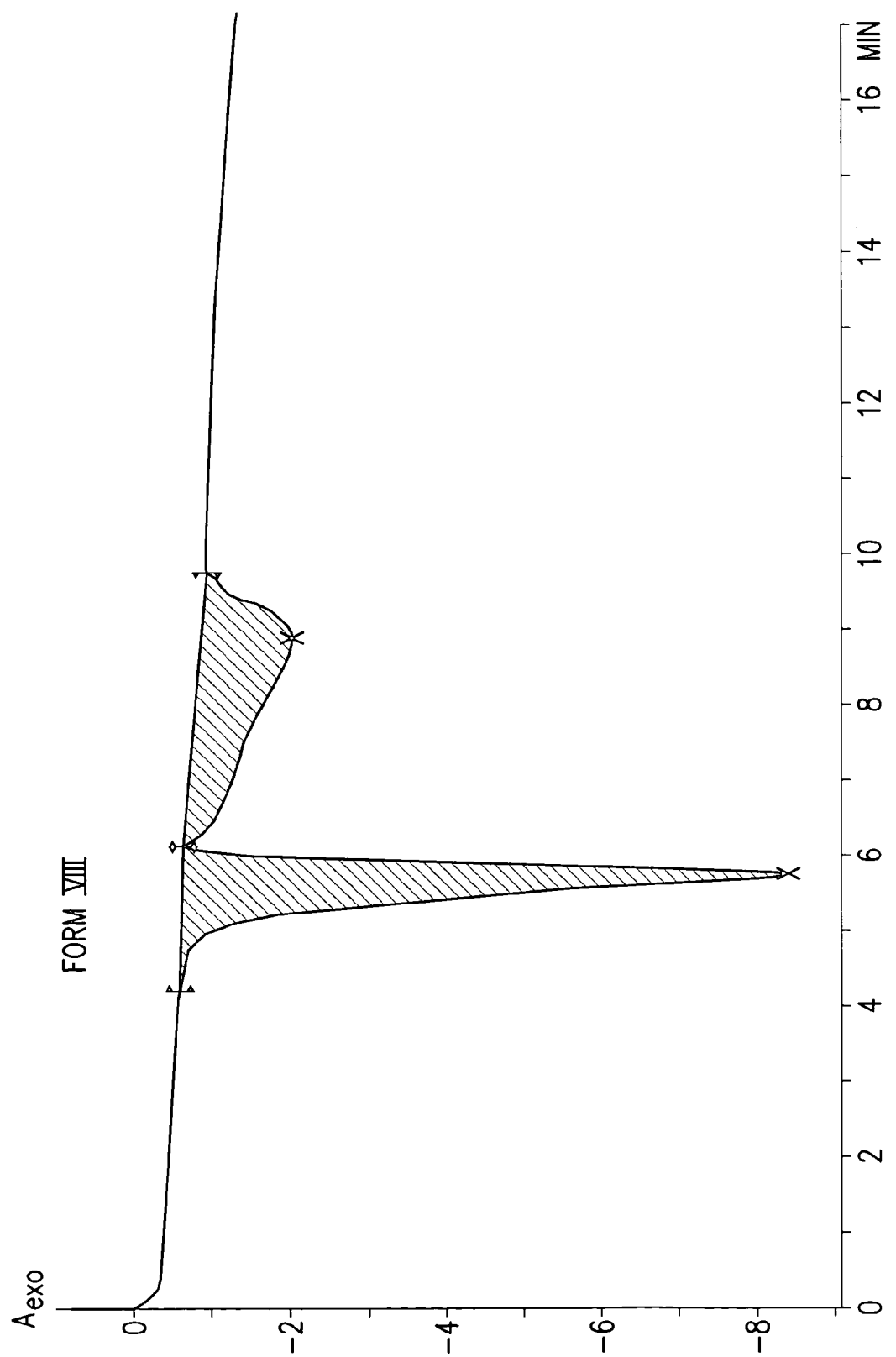
FIG. 14 illustrates the differential scan calorimetry analysis for Form VIII.

Yet another embodiment of the invention is a crystalline aripiprazole form, herein defined as Form VIII, having a weight loss of about 28% as measured by TGA, and a Karl Fisher analysis of about 0.5%. Form VIII may be characterized by X-ray powder diffraction peaks at 4.4, 8.7, 20.8, 21.6, and 26.0 degrees two-theta, ±0.2 degrees two-theta. Form VIII may be characterized further by X-ray powder diffraction peaks at 13.0, 17.3, 19.3, 24.5, 27.4, and 29.2 degrees two-theta, ±0.2 degrees two-theta. The typical DSC of Form VIII shows one endotherm at about 87° C. followed by a broad endotherm. Form VIII may be substantially identified by either the XRD pattern FIG. 4 or the DSC of FIG. 14.

Figure 5:
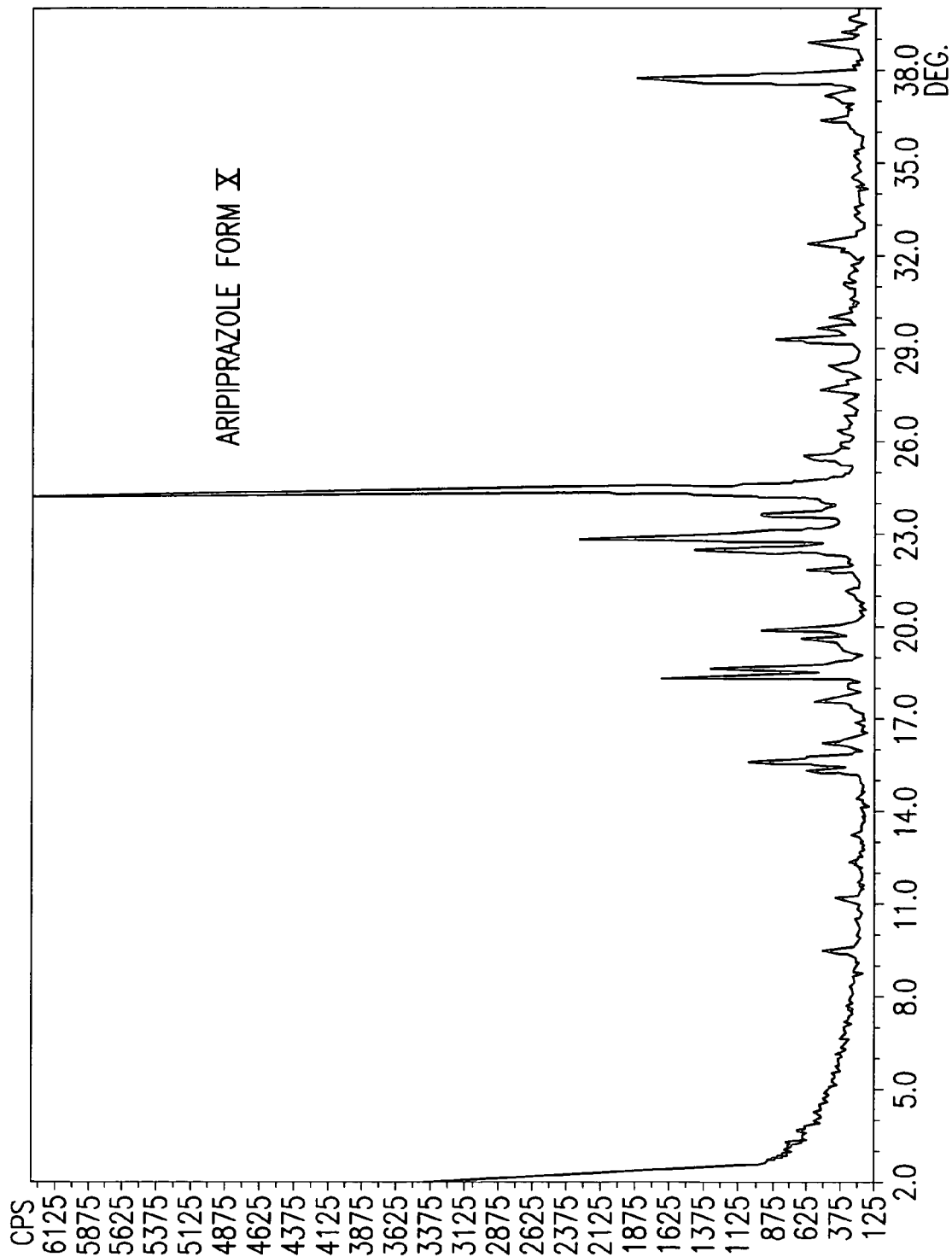
FIG. 5 illustrates the powder X-ray diffraction pattern for Form X.
Figure 15:
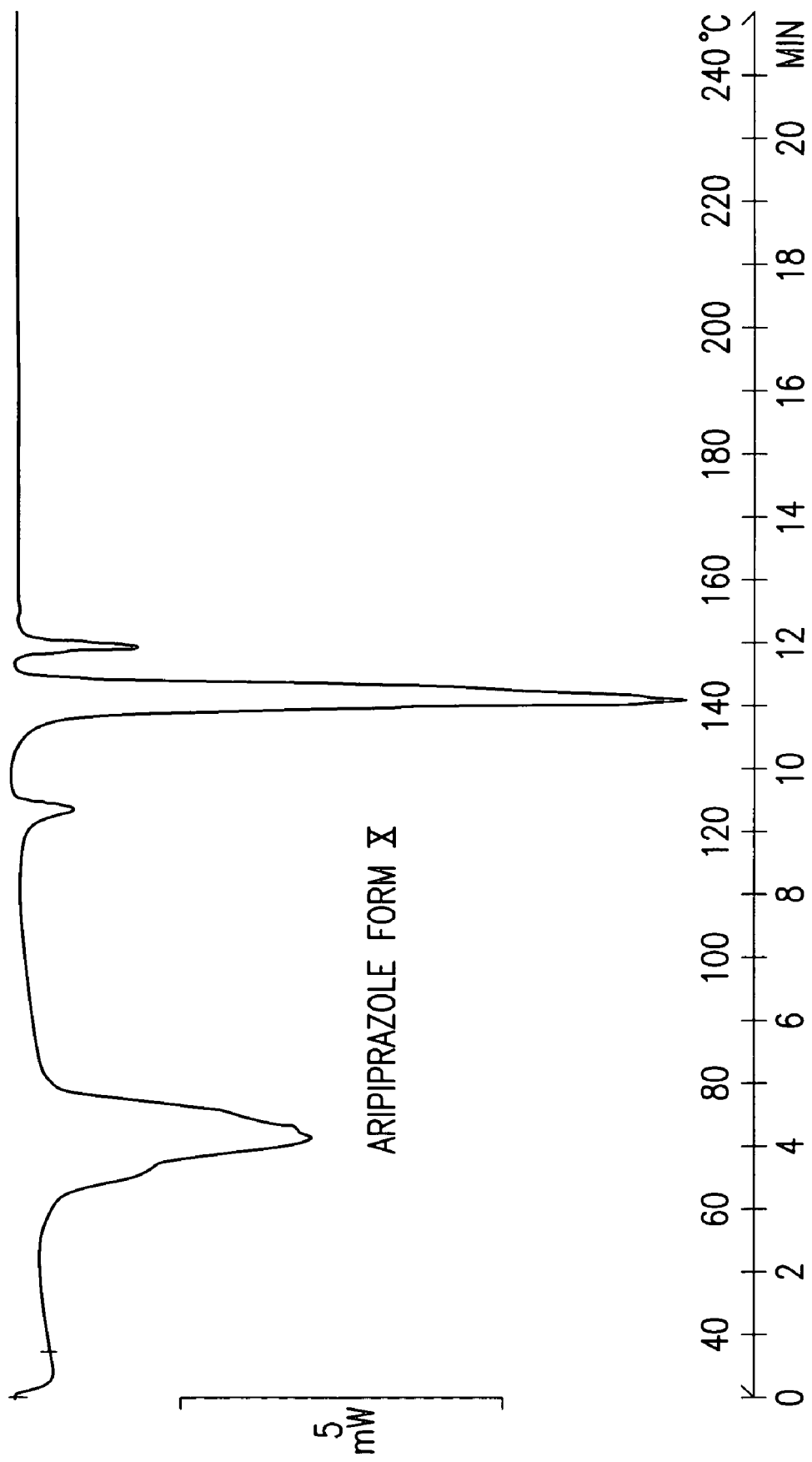
FIG. 15 illustrates the differential scan calorimetry analysis for Form X.

Another embodiment of the invention is a crystalline aripiprazole form, herein defined as Form X, having about 16% moisture by weight. Form X may be characterized by X-ray powder diffraction peaks at 18.2, 22.4, 22.8, and 24.3 degrees two-theta, ±0.2 degrees two-theta. Form X may be characterized further by X-ray powder diffraction peaks at 15.4, 19.8, 23.5, and 29.1 degrees two-theta, ±0.2 degrees two-theta. The typical DSC of Form X has an endotherm below about 100° C. Additionally, two endotherms appear at about 136° C. to about 140° C. and at about 147° C. to about 149° C. The first endotherm represents the transformation to crystalline Compound 2. The second endotherm represent the transformation to Form C. Form X may be substantially identified by either the XRD pattern of FIG. 5 or the DSC of FIG. 15.

Figure 6:
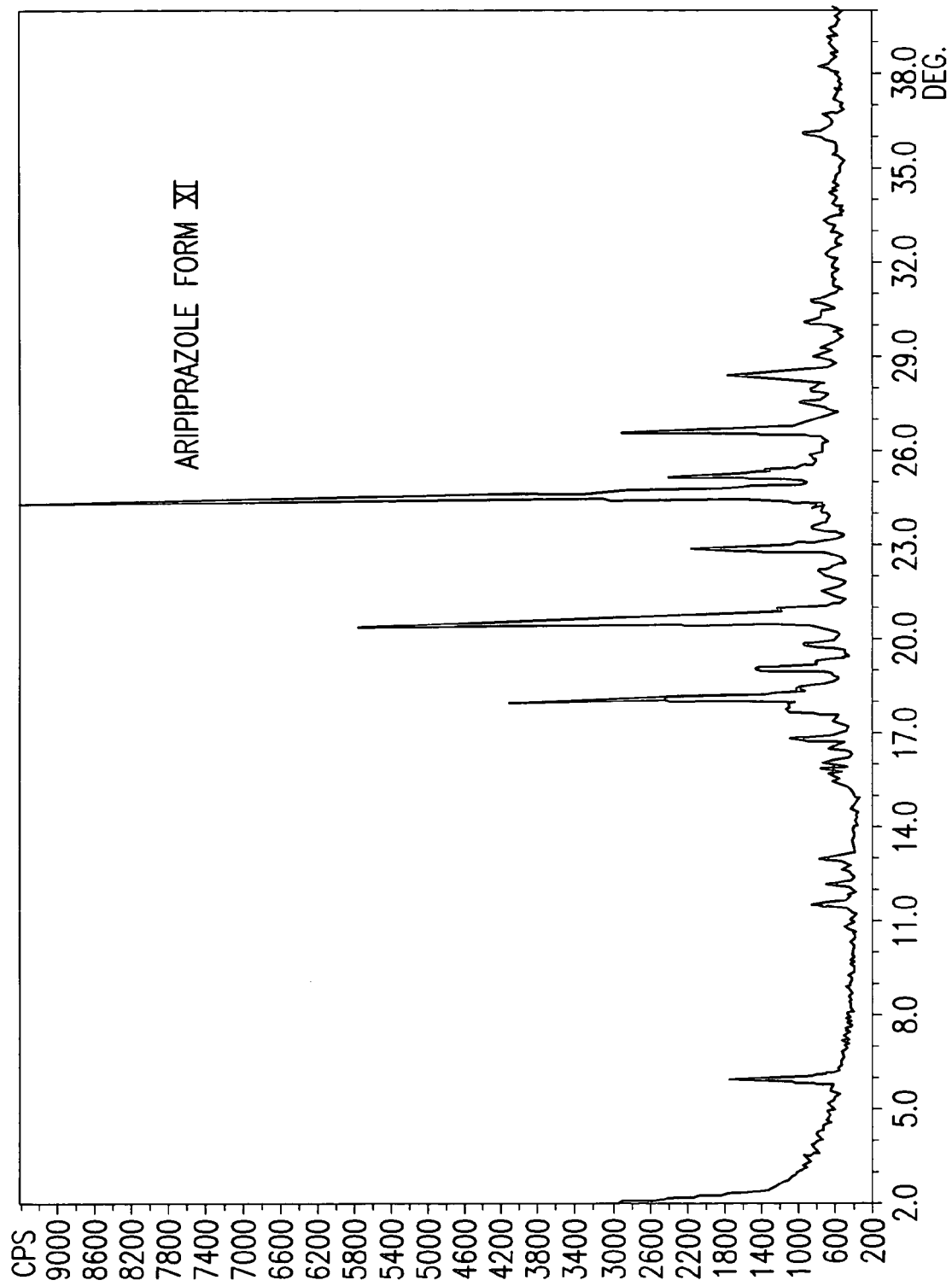
FIG. 6 illustrates the powder X-ray diffraction pattern for Form XI.
Figure 16:
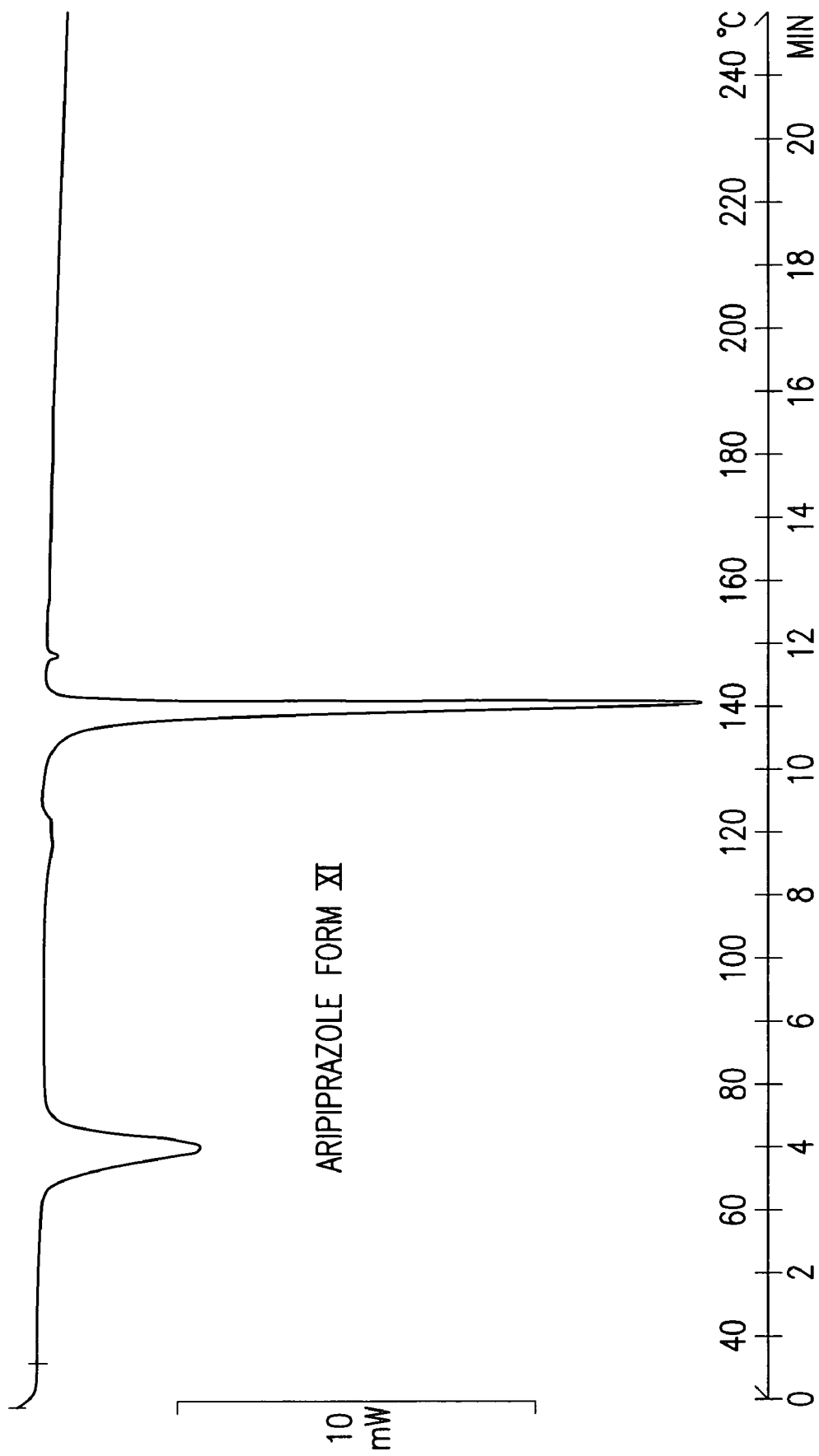
FIG. 16 illustrates the differential scan calorimetry analysis for Form XI.

Yet another embodiment of the invention is a crystalline aripiprazole form, herein defined as Form XI, having about 14% moisture by weight. Form XI may be characterized by X-ray powder diffraction peaks at 5.9, 18.0, 20.5, 24.5, and 25.1 degrees two-theta, ±0.2 degrees two-theta. Form XI may be characterized further by X-ray powder diffraction peaks at 19.0, 19.6, 22.7, 26.4, and 28.3 degrees two-theta, ±0.2 degrees two-theta. The typical DSC of Form XI shows an endotherm below about 100° C. and a melting endotherm at about 140° C. due to a transformation to crystalline Compound 2. Form XI may be substantially identified by either the XRD pattern of FIG. 6 or the DSC of FIG. 16.

Figure 8:
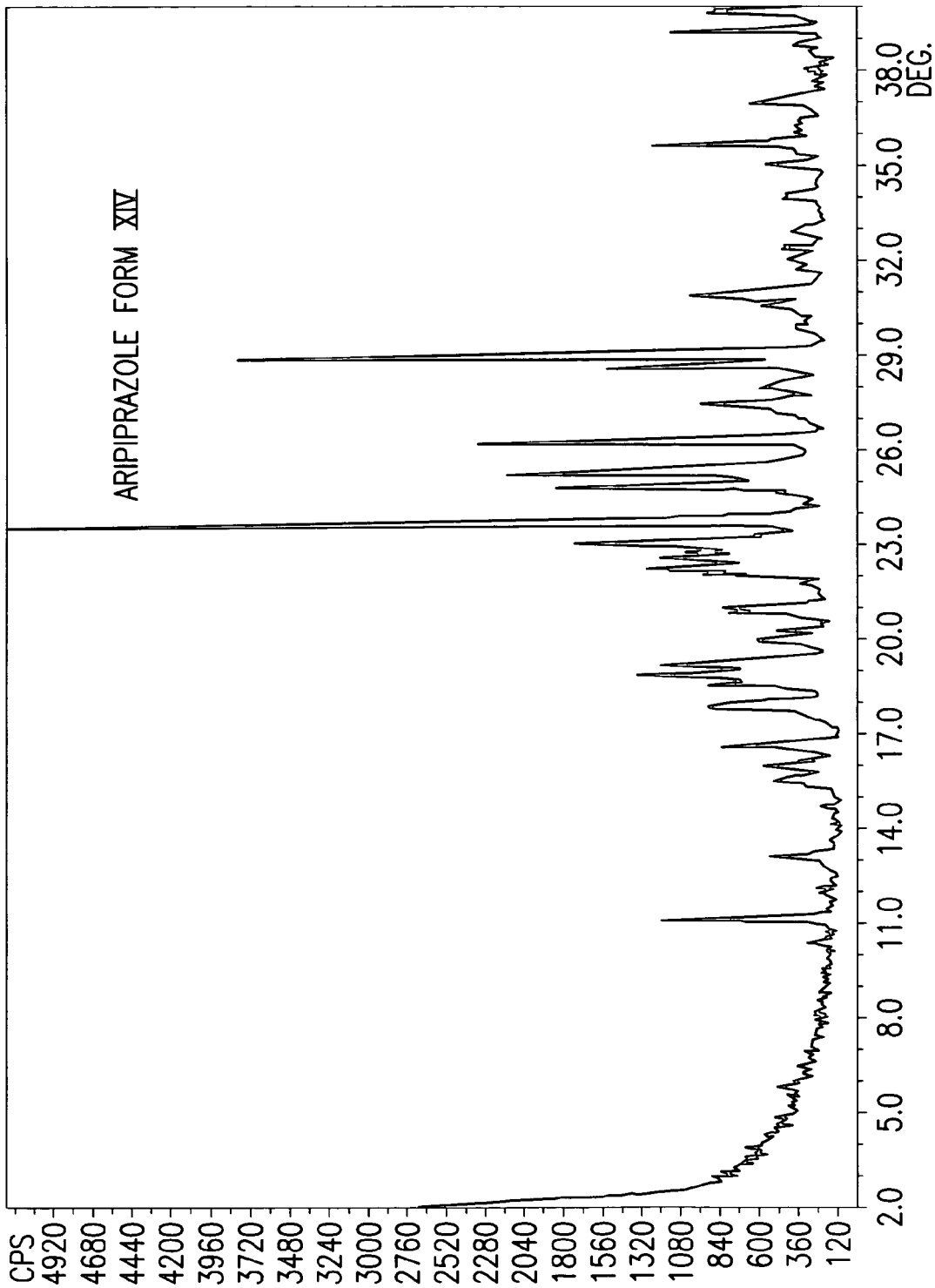
FIG. 8 illustrates the powder X-ray diffraction pattern for Form XIV.

Another embodiment of the invention is a crystalline aripiprazole form, herein defined as Form XIV, having about 9% weight loss as measured by TGA, and about 2% water content as measured by Karl Fisher. Form XIV may be characterized by X-ray powder diffraction peaks at 11.0, 23.6, 24.7, 25.2, and 29.0 degrees two-theta, ±0.2 degrees two-theta. Form XIV may be characterized further by X-ray powder diffraction peaks at 12.9, 16.5, 18.8, 22.2, 26.3, 27.3, and 28.5 degrees two-theta, ±0.2 degrees two-theta. Form XIV may be substantially identified by the XRD pattern of FIG. 8.

Figure 9:
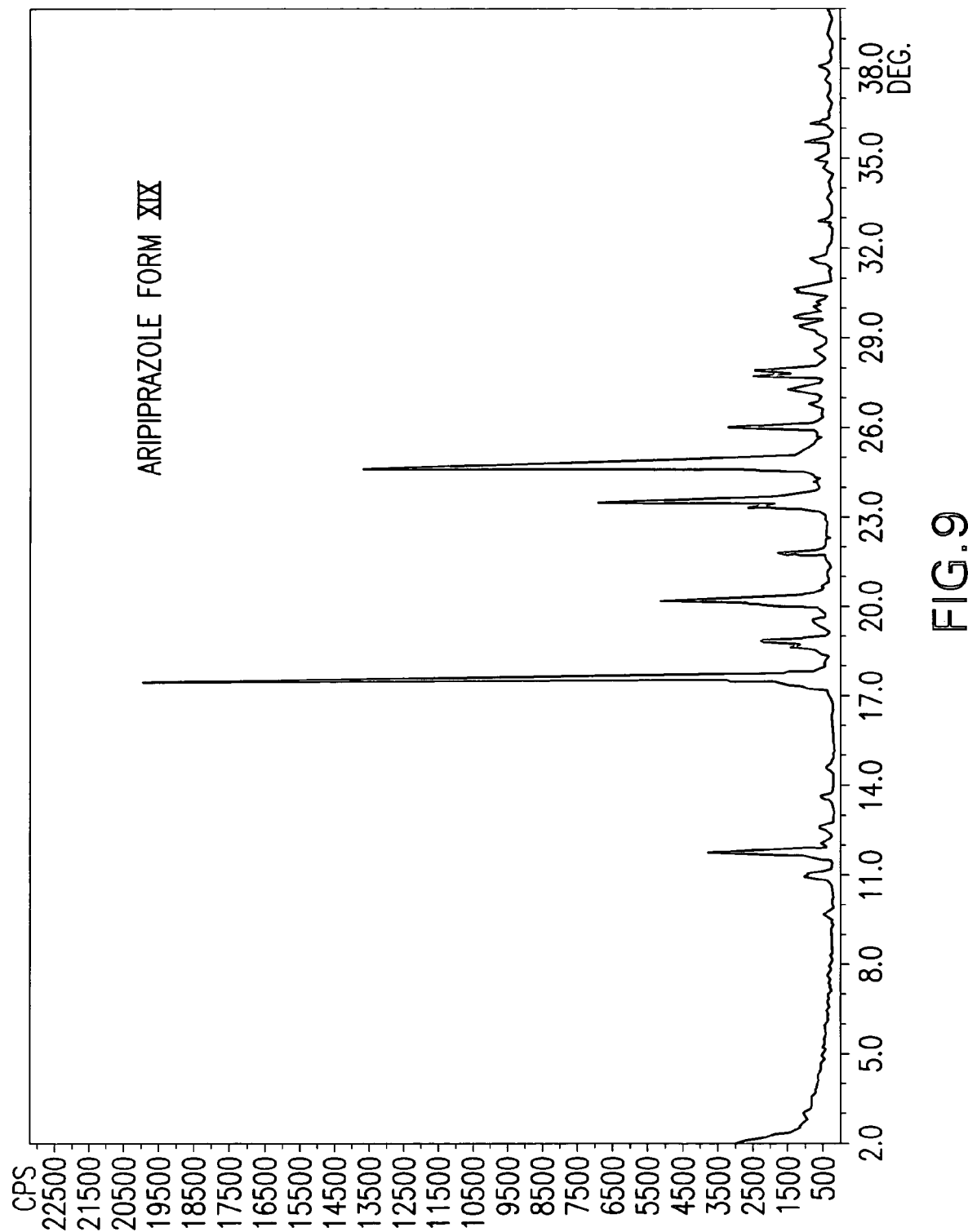
FIG. 9 illustrates the powder X-ray diffraction pattern for Form XIX.
Figure 17:
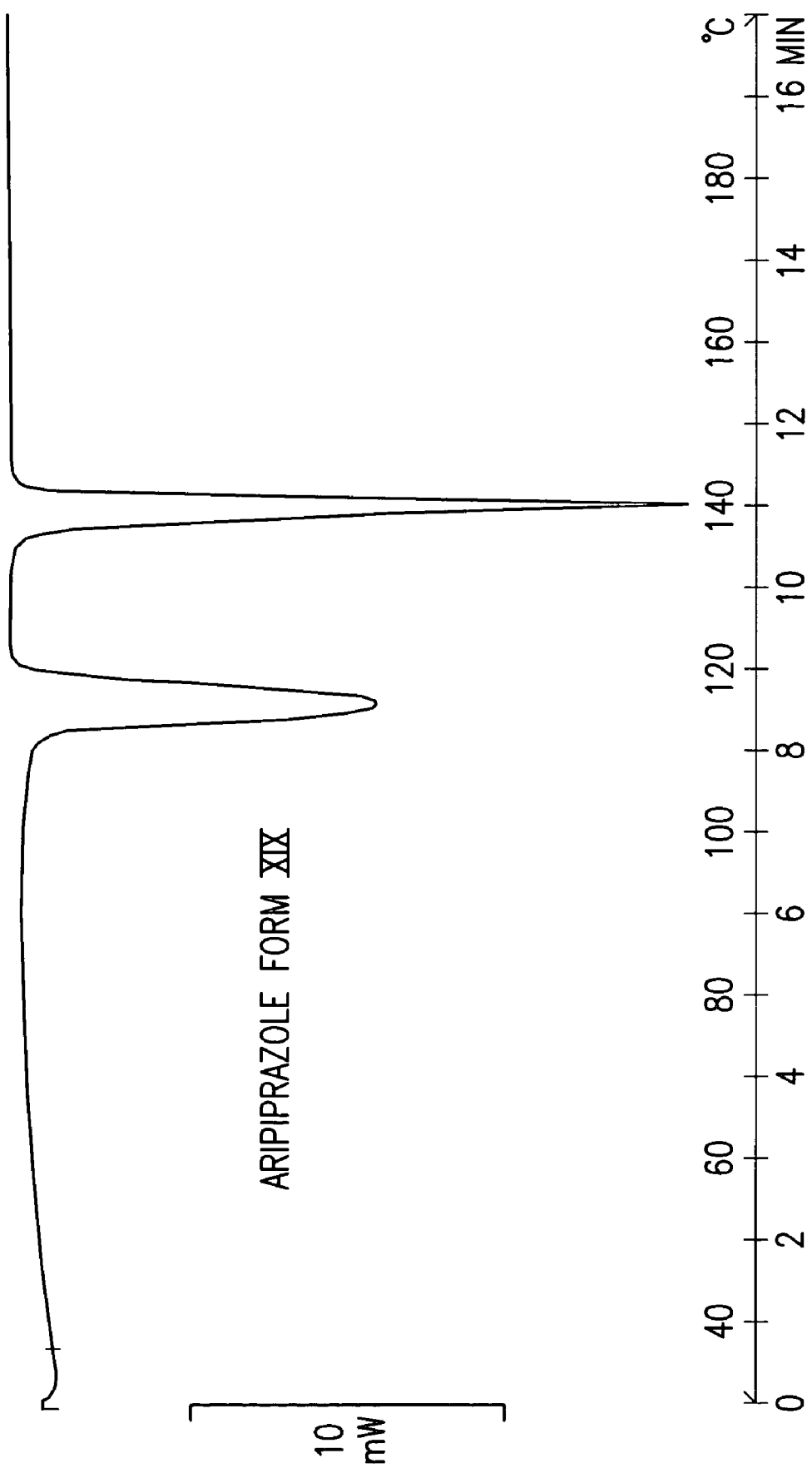
FIG. 17 illustrates the differential scan calorimetry analysis for Form XIX.

Another embodiment of the invention is a crystalline aripiprazole form, herein defined as Form XIX, having about 6% or less of moisture by weight as measured by Karl Fischer. Form XIX may be characterized by X-ray powder diffraction peaks at 17.4, 18.7, 20.0, 23.3, and 24.5 degrees two-theta, ±0.2 degrees two-theta. Form XIX may be characterized further by X-ray powder diffraction peaks at 10.8, 11.6, 27.1, 27.7, and 28.3 degrees two-theta, ±0.2 degrees two-theta. The typical DSC of Form XIX shows two endotherms, one at about 115° C., and one at about 140° C. Form XIX may be substantially identified by either the XRD pattern of FIG. 9 or the DSC of FIG. 17.

Figure 10:
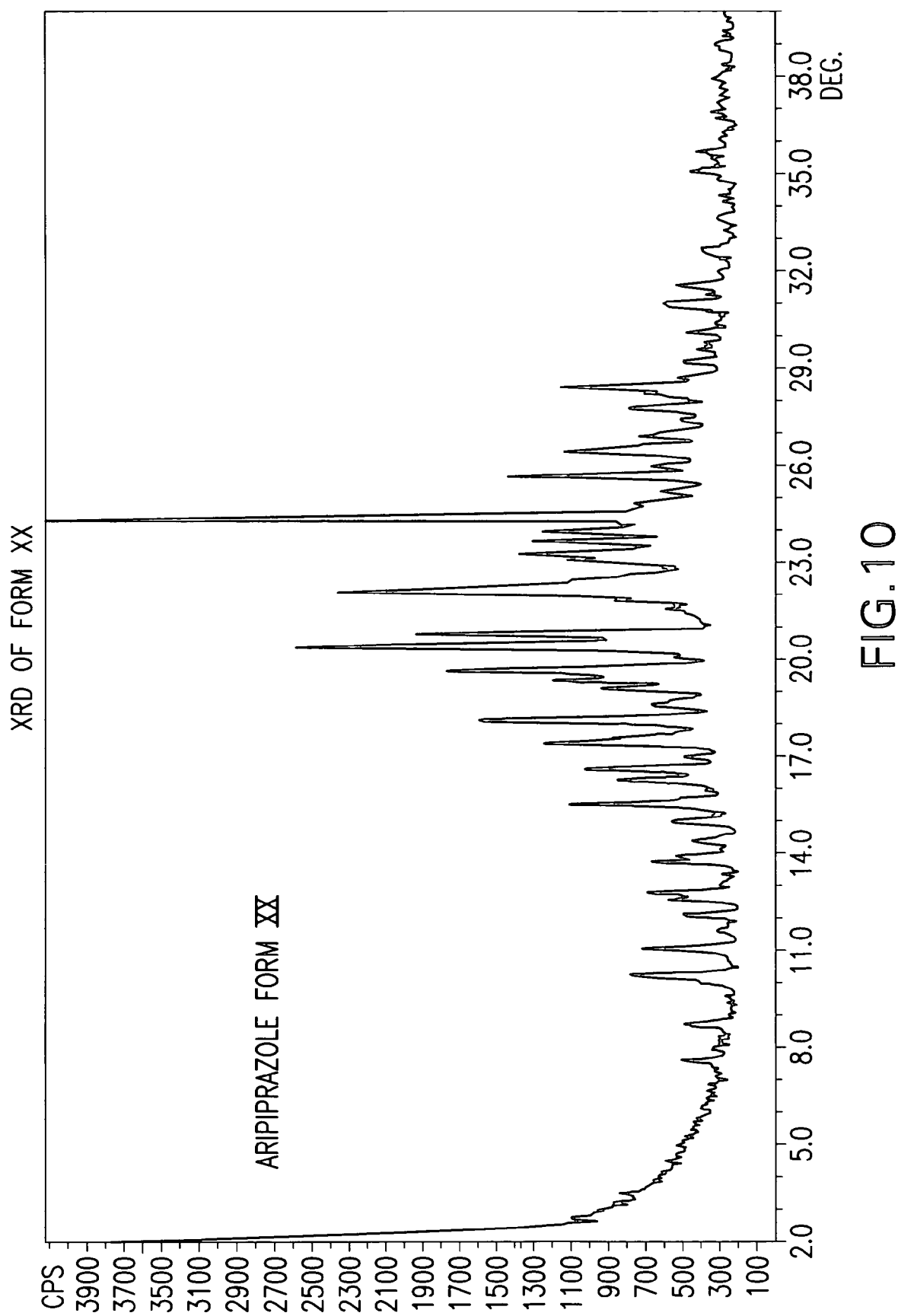
FIG. 10 illustrates the powder X-ray diffraction pattern for Form XX.
Figure 18:
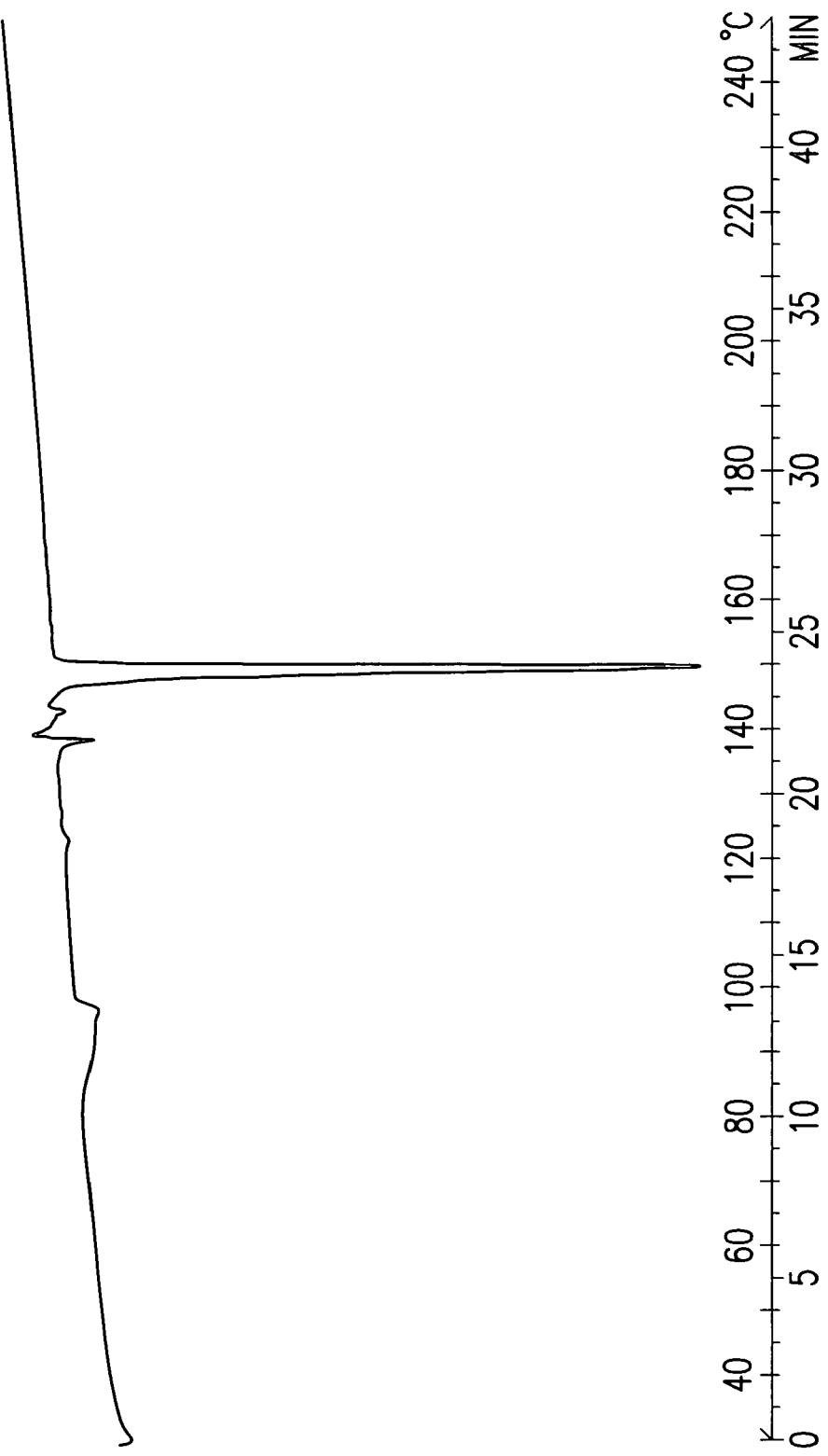
FIG. 18 illustrates the differential scan calorimetry analysis for Form XX.

Another embodiment of the invention is a crystalline aripiprazole form, herein defined as Form XX, having about 1.4% to about 5% moisture by weight as measured by Karl Fischer. Form XX may be characterized by X-ray powder diffraction peaks at 19.6, 20.4, 20.8, 22.1, and 24.5 degrees two-theta, ±0.2 degrees two-theta. Form XX may be characterized further by X-ray powder diffraction peaks at 10.2, 11.0, 15.6, 17.4, 18.2, 25.8, 26.6, and 28.5 degrees two-theta, ±0.2 degrees two-theta. The typical DSC of Form XX shows an endotherm at about 100° C., an endotherm at about 120° C., and multiple transitions between 140° C. and 150° C. Form XX may be substantially identified by either the XRD pattern of FIG. 10 or the DSC of FIG. 18.

The invention also encompasses methods of preparing Form I comprising providing Form X and drying Form X to obtain Form I.

The invention also encompasses methods of preparing Form II comprising providing crystalline Compound 1 and drying crystalline Compound 1 to obtain Form II.

Figure 19:
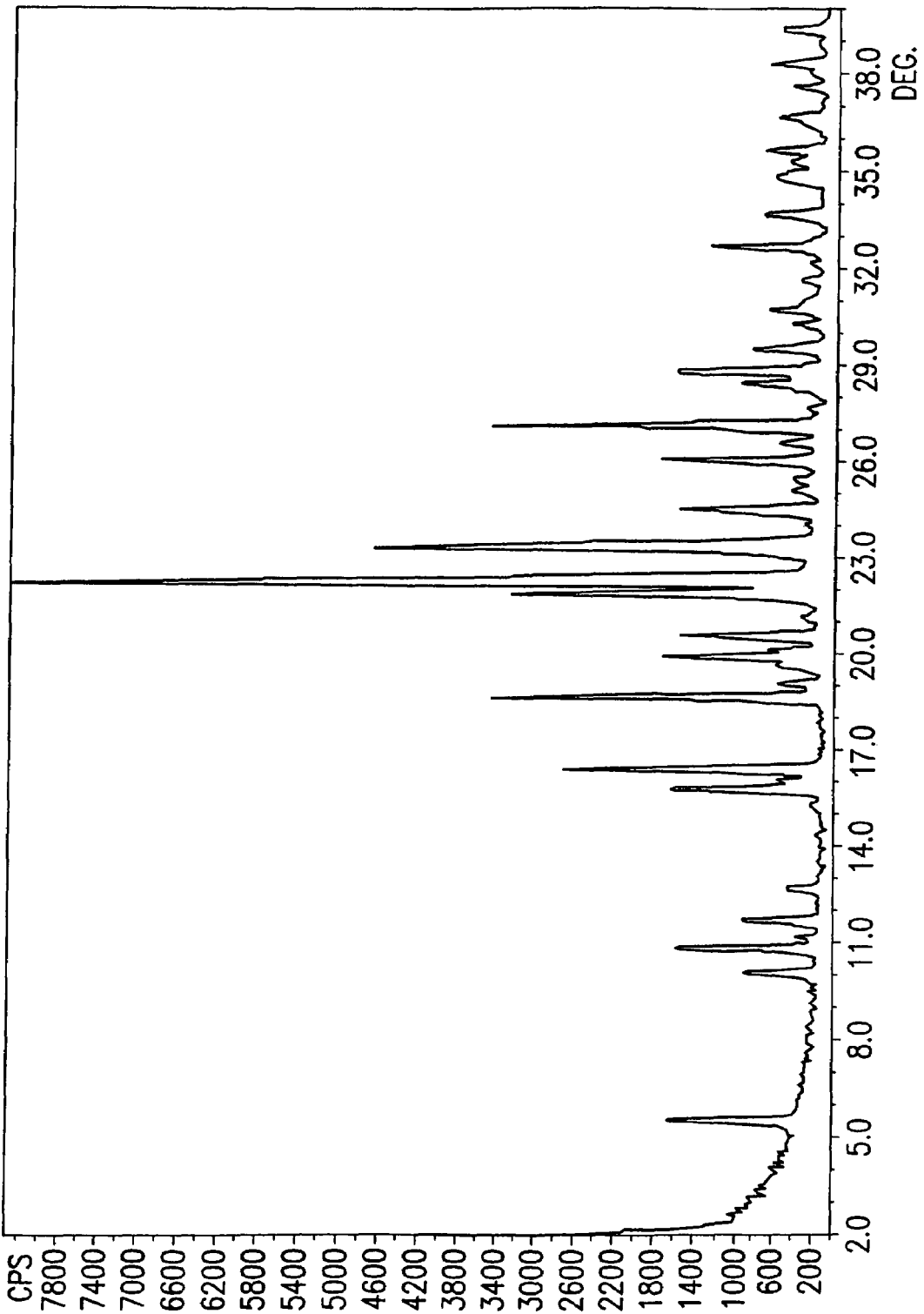
FIG. 19 illustrates the powder X-ray diffraction pattern for Form II obtained by slurrying aripiprazole crystalline Compound 2 with acetone.

The invention also encompasses a method for preparing Form II by slurrying crystalline Compound 2 in a sufficient amount of acetone for about one to about 24 hours until to obtain Form II and collecting Form II. Form II obtained by slurrying aripiprazole crystalline Compound 2 with acetone is substantially identified by the XRD of FIG. 19.

One of ordinary skill in the art with little or no experimentation can easily determine the sufficient amount of acetone depending upon the amount of aripiprazole crystalline Compound 2 used during the slurrying. Conditions that affect the amount of acetone include, but are not limited to, the amount of Form II to be crystallized and the purity of the starting crystalline Compound 2. Preferably, crystalline compound 2 is slurried for about three hours to about 24 hours, and more preferably for about five hours. Optionally, the process may further comprise drying the collected Form II at 50° C.

Form II may have a maximum particle size of about 300 microns or less.

The invention also encompasses methods for preparing aripiprazole crystalline Compound 1, crystalline Compound 2, Form D, Form I, Form II, Form VI, Form VIII, Form X, Form XI, or Form XII comprising dissolving aripiprazole in a solvent to form a mixture, heating the mixture to between about 40° C. and 132° C., cooling the mixture to form a precipitate, and collecting the precipitate. Preferably, the mixture is heated to about the lower of the boiling point of the solvent or aripiprazole's melting point before cooling. The mixture is preferably cooled to about 4° C. for a sufficient amount of time to form a precipitate. The resulting precipitate may be collected by any method commonly known in the art. Optionally, the method may further comprise drying the precipitate. Example 1 exemplifies the method described above. Table 1 summarized the results of the method.

Solvents which may be used in the method of the invention include, but are not limited to, $C_{3-6}$ ketones, $C_{1-4}$ nitriles, $C_{1-4}$ alcohols, $C_{1-6}$ halogenated alkanes, $C_{1-6}$ amines, $C_{2-8}$ amides, $C_{2-6}$ esters, $C_{2-6}$ ethers, $C_{1-6}$ sulfoxides, and $C_{4-10}$ aromatics. solvent is at least one of acetone, acetonitrile, trichloroacetonitrile, methanol, ethanol, n-propanol, isobutanol, propylene glycol, methyl-ethyl-ketone, tetrahydrofuran, DMF, piperidine, pyridine, xylene, toluene, cyclohexanamide, diethylamine, hexylamine, dimethylsulfoxide, ethyl acetate, butyl acetate, dichloromethane, dibromomethane, chloroform, 1-bromopropane, 1,4-dioxane, 1,2-diaminoethane, 1,4-dibromobutane, isopropanol, 1-butanol, 2-dimethylaminoethanol, cyclopropylmethylketone, or isobutlymethylketone.

The invention also encompasses methods for preparing crystalline compound 2 comprising dissolving aripiprazole in a solvent to form a mixture, heating the mixture to between about 40° C. and 132° C., cooling the mixture to form a precipitate, and collecting the precipitate. Preferably, the mixture of aripiprazole and solvent is heated to about the lower of the boiling point of the solvent or aripiprazole's melting point before cooling. The mixture is preferably cooled to about 4° C. for a sufficient amount of time to form a precipitate. The resulting precipitate may be collected by any method commonly known in the art. Optionally, the method may further comprise drying the precipitate. The method is exemplified in Example 1 and results are summarized in Table 1.

Solvents which may be used in the invention include, but are not limited to, $C_{3-6}$ ketones, $C_{1-4}$ nitriles, $C_{1-4}$ alcohols, $C_{1-6}$ halogenated alkanes, $C_{1-6}$ amines, $C_{2-8}$ amides, $C_{2-6}$ esters, $C_{2-6}$ ethers, $C_{1-6}$ sulfoxides, and $C_{4-10}$ aromatics. Preferably, the solvent is least one of chloroform, tetrahydrofuran, diethylamine, acetone, acetonitrile, piperidine, butylacetate, or DMF.

The amount of solvent added should be sufficient dissolve the amount of aripiprazole used. One of ordinary skill in the art with little or no experimentation can easily determine the sufficient amount of solvent. Conditions that affect the amount of solvent include, but are not limited to, the amount of aripiprazole to be crystallized and the purity of the starting aripiprazole.

A second method of the invention encompasses preparing crystalline Compound 1, crystalline Compound 2, Form II, Form XII, or Form XIX by dissolving aripiprazole in a solvent to form a mixture, heating the mixture to the solvent's boiling point to dissolve aripiprazole, adding a co-solvent to precipitate aripiprazole, cooling the co-solvent mixture to about room temperature to about 4° C., and collecting the precipitate. The second method may further comprise cooling the mixture before adding the co-solvent if the boiling point of the co-solvent is lower than the boiling point of the solvent.

Preferably, the co-solvent mixture is left at about 4° C. for 15 hours before collecting the precipitate. The precipitate may be collected by any method commonly known in the art. Optionally, the process may further comprise drying the precipitate, preferably under reduced pressure of less than about 100 mm Hg at 35° C.

As described above, one of ordinary skill in the art can easily determine the amount of solvent necessary to dissolve aripiprazole. Solvents that may be used in the second method of the invention include, but are not limited to, $C_{2-6}$ esters, $C_{2-6}$ ethers, methylethylketones, or $C_{1-6}$ halogenated alkanes. Preferably, the solvent is at least one of ethyl acetate, methylethylketone, chloroform, or tetrahydrofuran.

The co-solvent of the second method should be added in an amount sufficient to precipitate aripiprazole from solution. Co-solvents that may be used in the second method of the invention include, but are not limited to, at least one of water, $C_{1-4}$ alcohols, $C_{2-6}$ ether, or acetone. Preferably, the co-solvent is at least one of acetone, water, methanol, ethanol, ether, or 2-propanol.

A second method of preparing aripiprazole crystalline compound 2 encompasses dissolving aripiprazole in a solvent to form a mixture, heating the mixture to the solvent's boiling point to dissolve aripiprazole, adding a co-solvent until aripiprazole precipitates, cooling the mixture to about room temperature to about 4° C., and collecting the precipitated crystalline compound 2. The second method may further comprise cooling the aripiprazole solvent mixture before adding co-solvent if the boiling point of the co-solvent is lower than the boiling point of the solvent.

Preferably, the mixture is left at about 4° C. for 15 hours before collecting the precipitated aripiprazole. The precipitate may be collected by any method commonly known in the art. Optionally, the process may further comprise drying the precipitate, preferably under reduced pressure of less than about 100 mmHg at 35° C.

As indicated above, one of ordinary skill in the art can easily determine the amount of solvent necessary to dissolve aripiprazole. Solvents that may be used in the second method of the invention include, but are not limited to, $C_{2-6}$ esters, $C_{2-6}$ ethers, methylethylketones, and $C_{1-6}$ halogenated alkanes. Preferably, the solvent is tetrahydrofuran.

Co-solvent is added in an amount sufficient to precipitate aripiprazole from solution. Co-solvents that may be used in the second method of the invention include, but are not limited to, water, $C_{1-4}$ alcohols, $C_{2-6}$ ether, or acetone. Preferably, the co-solvent is at list one of acetone, ether, or 2-propanol.

The temperature at which the co-solvent is added depends on the boiling point of the co-solvent. If the boiling point for the co-solvent is lower than the boiling point of the solvent, then the mixture is cooled to the boiling point of the co-solvent before adding the co-solvent. If a precipitate appears while lowering the temperature prior to addition of the co-solvent, then additional solvent should be added in an amount sufficient to dissolve the precipitate. Co-solvent is then added in an amount sufficient to precipitate aripiprazofe. Example 2 exemplifies the second method. Table 2 summarizes the results of the second method.

The invention also encompasses methods of preparing Form I by drying Form X under a pressure of less than about 100 mm Hg at 35° C. until Form I is formed.

The invention also encompasses methods of preparing Form II by drying crystalline Compound 1 at a pressure of less than about 100 mm Hg at 35° C. until Form II is formed.

The invention also encompasses methods of preparing crystalline Compound 2 comprising providing at least one Form D, Form X, Form XI, Form XII, or Form XIX, and heating to form crystalline Compound 2.

Preferably, the heating step is performed at about 100° C. to about 130° C. for about 30 to about 60 minutes. The preparation of crystalline Compound 2 by heating crystalline Form D, Form X, Form XI, Form XII, or Form XIX may involve an intermediate transformation to Form D. For example, crystalline Compound 1 transforms to Form D after heating to 100° C. for 60 minutes; however, additional heating at 130° C. for 30 minutes completes the conversion of crystalline Compound 1 into crystalline Compound 2.

The invention also encompasses methods of preparing crystalline Compound 2 comprising providing Form XI and drying at a pressure of less than about 100 mm Hg at 35° C. to form crystalline Compound 2.

The invention also encompasses methods of preparing crystalline Compound 2 by adding Form XII to a reactor at a temperature of about 25° C. to about 35° C. at a pressure of 100 mm Hg or less, preferably at a pressure of 60 mm Hg or less, and gradually increasing the temperature to about 100° C. or less, while stirring at about 12 rpm, until crystalline Compound 2 is obtained. Preferably, the crystalline Compound 2 contains no more than 5% of crystalline Form C, Form D, or Form XII.

The invention also encompasses methods of preparing Form C comprising providing at least one of Form II, crystalline Compound 1, or crystalline Compound 2, and heating to form Form C. Preferably, the crystalline form is heated at about 130° C. to about 145° C. for about 30 to about 180 minutes. Small increases in temperature may have a significant effect on the time required for the formation of Form C.

The invention also encompasses methods of preparing Form D comprising providing at least one of crystalline Compound 1, crystalline Compound 2, or Form XIV, and drying the crystalline form at a pressure of less than about 100 mm Hg at 35° C. to form Form D.

The invention also encompasses methods of preparing a mixture of crystalline Compound 2 and crystalline Compound 1 comprising providing Form XI and drying at a pressure of less than about 100 mm Hg at 35° C. to form a mixture crystalline Compound 2 and crystalline Compound 1.

The invention also encompasses methods of preparing a mixture of Form D, crystalline Compound 1, and crystalline Compound 2 comprising providing a mixture of Form D and Compound 1, and drying the mixture at a pressure of less than about 100 mm Hg 35° C. to form a mixture of Form D, crystalline Compound 1, and crystalline Compound 2.

The invention also encompasses methods of preparing Form XII comprising adding aripiprazole and ethanol (95% by volume) to form a mixture, heating the mixture at reflux until aripiprazole dissolves while mechanically stirring the mixture at 12 rpm, filtering the mixture, cooling the mixture to 0° C. over 6 hours, stirring the mixture for one hour, filtering the mixture, and washing with one volume of ethanol (95% by volume). Form XII is obtained.

The invention also encompasses methods of preparing Form XX comprising placing Form XII into a fluidized bed dryer at about 30° C., leaving the material for about 3.5 hours at 30° C. to obtain a crystalline form, and drying the crystalline form at about 40° C. until Form XX is formed.

Tables 1, 2, and 3 summarize the conversion of crystalline forms of the invention.

The invention also encompasses pharmaceutical compositions comprising aripiprazole crystalline forms of the invention. As used herein, the term "pharmaceutical compositions" includes tablets, pills, powders, liquids, suspensions, emulsions, granules, capsules, suppositories, or injection preparations. Pharmaceutical compositions containing the aripiprazole crystalline forms of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Any excipient commonly known and used widely in the art can be used in the pharmaceutical composition. Carriers used include, but are not limited to, lactose, white sugar, sodium chloride, glucose, urea, starch, calcium carbonate, kaolin, crystalline cellulose, silicic acid, and the like. Binders used include, but are not limited to, water, ethanol, propanol, simple syrup, glucose solutions, starch solutions, gelatin solutions, carboxymethyl cellulose, shelac, methyl cellulose, potassium phosphate, polyvinylpyrrolidone, and the like. Disintegrating agents used include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, and the like. Disintegration inhibitors used include, but are not limited to, white sugar, stearin, coconut butter, hydrogenated oils, and the like. Absorption accelerators used include, but are not limited to, quaternary ammonium base, sodium laurylsulfate, and the like. Wetting agents used include, but are not limited to, glycerin, starch, and the like. Adsorbing agents used include, but are not limited to, starch, lactose, kaolin, bentonite, colloidal silicic acid, and the like. Lubricants used include, but are not limited to, purified talc, stearates, boric acid powder, polyethylene glycol, and the like. Tablets can be further coated with commonly known coating materials such as sugar coated tablets, gelatin film coated tablets, tablets coated with enteric coatings, tablets coated with films, double layered tablets, and multi-layered tablets.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohols, esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic.

Additional ingredients, such as dissolving agents, buffer agents, and analgesic agents may be added. If necessary, coloring agents, preservatives, perfumes, seasoning agents, sweetening agents, and other medicines may also be added to the desired preparations.

The amount of aripiprazole or salt thereof contained in a pharmaceutical composition for treating schizophrenia should be sufficient to treat, ameliorate, or reduce the symptoms associated with schizophrenia. Preferably, aripiprazole is present in an amount of about 1% to about 70% by weight, and more preferably from about 1% to about 30% by weight of the dose.

The pharmaceutical compositions of the invention may be administered in a variety of methods depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations may be administered intramuscularly, intracutaneously, subcutaneously or intraperitoneally. Suppositories may be administered into the rectum.

The dosage of a pharmaceutical composition for treating schizophrenia according to the invention will depend on the method of use, the age, sex, and condition of the patient. Preferably, aripiprazole is administered in an amount from about 0.1 mg/kg to about 10 mg/kg of body weight/day. More preferably, about 1 mg to 200 mg of aripiprazole may be contained in a dose.

The invention also encompasses methods of making a pharmaceutical formulation comprising adding at least one of aripiprazole crystalline compound 1, crystalline Form I, II, VI, VIII, X, XI, XII, XIV, XIX, or XX, and a pharmaceutically acceptable excipient. As used herein, the term "pharmaceutical formulations" includes tablets, pills, powders, liquids, suspensions, solutions, emulsions, granules, capsules, suppositories, or injection preparations.

Having described the invention with reference to certain preferred embodiments, other embodiments will become apparent to one skilled in the art from consideration of the specification. The invention is further defined by reference to the following examples describing in detail the analysis of the aripiprazole crystalline forms and methods for preparing the crystalline forms of the invention. It will be apparent to those skilled in the art that many modifications, both to materials and methods, may be practiced without departing from the scope of the invention.

EXAMPLES

X-ray powder diffraction data were obtained using a SCIN-TAG powder X-ray diffractometer model X'TRA equipped with a solid state detector and copper radiation of 1.5418 Å. A round aluminum sample holder with zero background was used. All peak positions are within ±0.2 degrees two theta. Differential scan calorimetry (DSC) analysis was performed using a Mettler 821 Stare differential scanning calorimeter. The weight of the samples was about 3 mg to about 6 mg. The samples were scanned at a rate of 10° C./min from 30° C. to at least 200° C. The oven was constantly purged with nitrogen gas at a flow rate of 40 ml/min. Standard 40 μl aluminum crucibles covered by lids with 3 holes were used.

Thermogravimetric analysis (TGA) was performed using a Mettler M3 thermogravimeter. The samples weighed about 10 mg and were scanned at a rate of 10° C./min from 25° C. to 200° C. The oven was constantly purged with nitrogen gas at a flow rate of 40 ml/min. Standard 150 μl alumina crucibles covered by lids with 1 hole were used.

Karl Fisher analysis was performed according to methods well known in the art.

Example 1

Preparation of Aripiprazole Polymorphs

Aripiprazole (4 g) was dissolved in solvent in a round bottomed flask (50-250 ml), and heated to the lower of the solvent's boiling point or to aripiprazole's melting point and stirred until the aripiprazole fully dissolved. The immersion obtained was cooled to room temperature, and then left at 4° C. for 15 hours. The precipitated crystalline form was collected by filtration and studied by X-Ray Diffraction Technique (XRD). The crystalline form was then dried under reduced pressure of less than about 100 mm Hg at 35° C. and again studied by XRD. The results are summarized in Table 1.

TABLE 1

Crystallization of Aripiprazole Crystalline forms Using Method 1

| Solvent/s | Volume (ml) | Temp. (° C.) | Wet (w)/ Dry (d) | Resulting Crystalline Form[a] |
|---|---|---|---|---|
| Dichloromethane | 19 | 40 | w | X |
|  |  |  | d | I |
| Chloroform | 5 | 61 | w | II |
|  |  |  | d | II |
| Tetrahydrofuran | 6 | 66 | w | II |
|  |  |  | d | II |
| 1-Bromopropane | 32 | 71 | w | Compound 2 |

TABLE 1-continued

Crystallization of Aripiprazole Crystalline forms Using Method 1

| Solvent/s | Volume (ml) | Temp. (° C.) | Wet (w)/ Dry (d) | Resulting Crystalline Form[d] |
|---|---|---|---|---|
| Methylethylketone | 17 | 80 | d | Compound 2 |
| | | | w | Compound 1 + Compound 2 |
| | | | d | Compound 2 |
| Trichloroacetonitrile | 8 | 83-84 | w | I |
| | | | d | I |
| Dibromomethane | 5 | 96-98 | w | XI |
| | | | d | Compound 1 + Compound 2 |
| 1,4-Dioxane | 6 | 100-102 | w | Compound 1 + Compound 2 |
| | | | d | hydrate + compound 2 |
| Diethylamine | 110 | 55 | w | II |
| | | | d | II |
| Acetone | 90 | 56 | w | II |
| | | | d | II |
| Ethyl acetate | 45 | 77 | w | Compound 1 + Form D |
| | | | d | Compound 1 + Form D |
| 2-Propanol | 80 | 82 | w | Compound 1 + Form D |
| | | | d | Compound 1 + Form D + Compound 2 |
| Acetonitrile | 165 | 81-82 | w | II |
| | | | d | II |
| Piperidine | 4 | 106 | w | II |
| | | | d | II + Compound 2 |
| Isobutanol | 4 | 108 | w | Compound 1 |
| | | | d | D |
| Toluene | 4 | 110.6 | w | Compound 1 + Compound 2 |
| | | | d | Compound 2 |
| Cyclopropylmethyl ketone | 3 | 114 | w | Compound 1 + Compound 2 |
| | | | d | Compound 1 + Form D |
| Pyridine | 4 | 115-116 | w | XIV |
| | | | d | Form D |
| 1-Butanol | 8 | 118 | w | Compound 1 |
| | | | d | Compound 1 + Compound 2 |
| Isobutylmethyl ketone | 7 | 116.5 | w | Compound 1 + Compound 2 |
| | | | d | Compound 2 |
| Butylacetate | 4 | 124-126 | w | II |
| | | | d | II |
| Xylene | 3 | 132 | w | Form D |
| | | | d | Form D |
| DMF | 5 | 132 | w | II |
| | | | d | II |
| Cyclohexanone | 3 | 132 | w | Compound 1 |
| | | | d | Form D |
| Bromobenzene | 4 | 132 | w | Compound 1 |
| | | | d | Compound 2 |
| 3-Amino-1-propanol | 5.5 | 132 | w | Compound 2 |
| | | | d | Compound 2 |
| Dimethylsulfoxide | 4 | 132 | w | VIII |
| | | | d | VIII |
| Propylene glycol | 3 | 132 | w | VI |
| | | | d | VI |
| Chlorobenzene | 4 | 132 | w | Compound 1 + Form D |
| | | | d | D |
| Cyclohexanamide | 3.5 | 134 | w | Compound 1 + Form D |
| | | | d | D |
| 2-Dimethylamino ethanol | 4 | 132 | w | Compound 1 + Compound 2 |
| | | | d | Form D |
| 1,2-Diaminoethane | 4 | 118 | w | Form D |

TABLE 1-continued

Crystallization of Aripiprazole Crystalline forms Using Method 1

| Solvent/s | Volume (ml) | Temp. (° C.) | Wet (w)/ Dry (d) | Resulting Crystalline Form[d] |
|---|---|---|---|---|
| | | | d | Form D |
| Hexylamine | 4 | 131-132 | w | Compound 1 + Compound 2 |
| | | | d | Compound 2 |
| 1,4-Dibromobutane | 4 | 132 | w | Am + Form D |
| | | | d | Am + Form D |
| Ethanol | 68 | 78 | w | XII* |
| | | | d | XII* |
| Ethanol 95% in water | 80 | 78 | d | XII* |
| Ethanol 80% in water | 160 | 78 | w | Compound 1 |
| | | | d | Compound 1 |
| Acetone[b] | 90 | 56 | w | II > Form D |
| Chloroform[b] | 10 | 61 | w | Form D |
| | | | d | Form D |
| Ethyl Acetate[b] | 50 | 77 | d | Compound 2 |
| | 10 | 110.6 | d | Compound 2 |

[a]Aripiprazole MP = 132° C.

[b]Solvent was immediately evaporated after aripiprazole's dissolution.

[c]Traces of Form B were present.

[d]"Compound 1" is "crystalline Compound 1" and "Compound 2" is "crystalline Compound 2."

Figure 7:
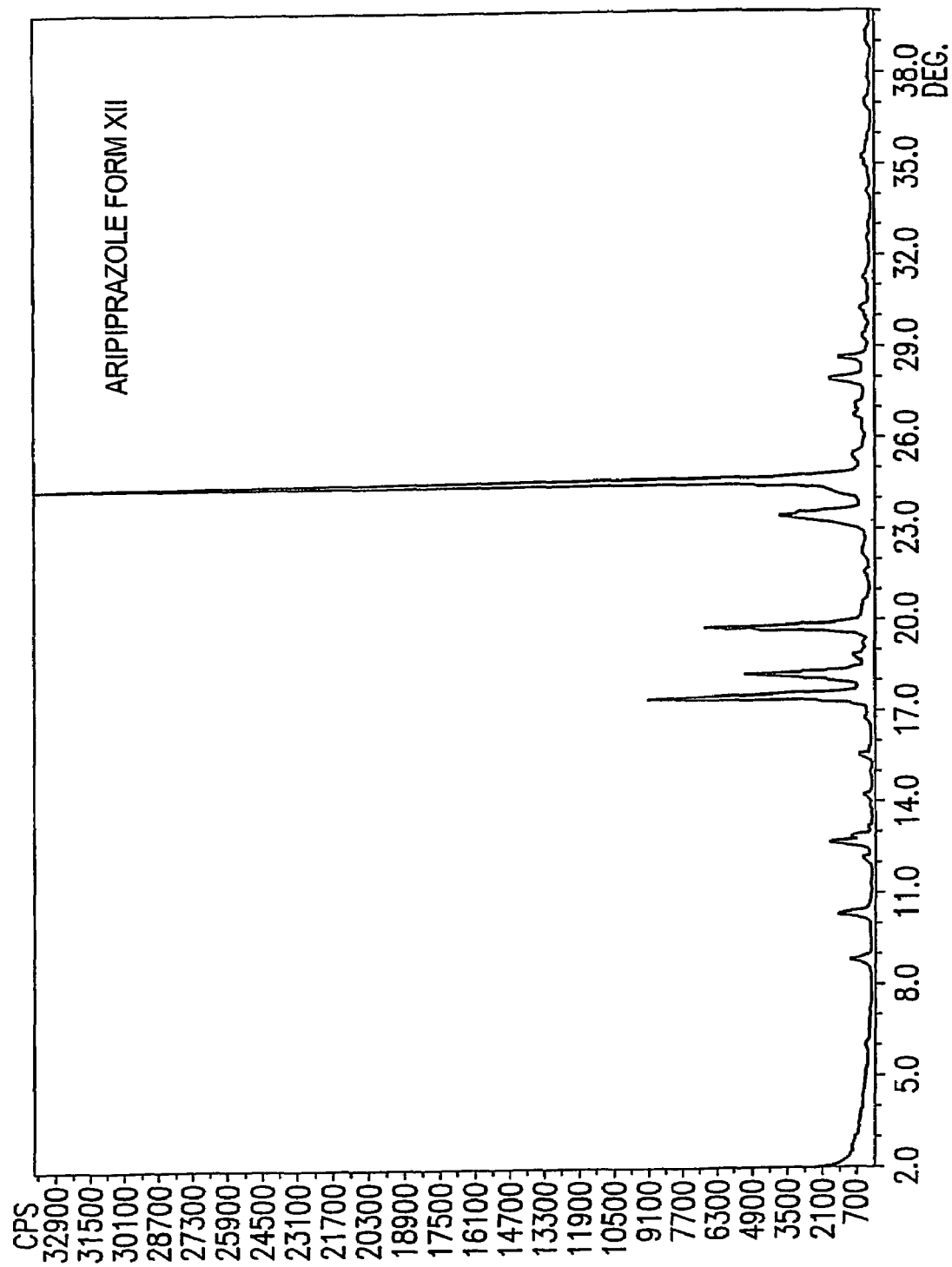
FIG. 7 illustrates the powder X-ray diffraction pattern for Form XII.

* Form XII may be characterized by X-ray powder diffraction peaks at 17.4, 18.2, 19.7, and 24.5 degrees two-theta, ±0.2 degrees two-theta as depicted in the XRD of FIG. 7.

Example 2

Preparation of Aripiprazole Crystalline forms Using Co-Solvent Systems

Aripiprazole (4 g) was dissolved in a given solvent in a round bottomed flask (50-250 ml), and heated to the solvent's boiling point until aripiprazole fully dissolved. The temperature was cooled to the boiling point of the co-solvent to be used if this temperature was lower than the boiling point of the solvent used to dissolve aripiprazole. If a precipitate formed during cooling, then additional solvent was added until the precipitate dissolved. Co-solvent was then added until a precipitate formed.

The immersion obtained was cooled to room temperature, and left at 4° C. for 15 hours. The resulting crystalline form was collected by filtration and studied by XRD. The crystalline form was then dried under reduced pressure of less than about 100 mm Hg at 35° C. and again studied by XRD. The results are summarized in Table 2.

TABLE 2

Crystallization of Aripiprazole Crystalline forms by Method 2

| Solvent | Volume (ml) | Temp. (° C.) | Co-Solvent | Volume (ml) | Wet (w)/dry (d) | Resulting Crystalline Form |
|---|---|---|---|---|---|---|
| Ethyl Acetate | 45 | 77 | Methanol | 12 | w | XII* |
|  |  |  |  |  | d | XII* |
| Ethyl Acetate | 45 | 77 | Ethanol | 50[a] | w | XIX |
|  |  |  |  |  | d | XIX |
| Methylethyl ketone | 22 | 80 | Acetone | 2.5 | w | Compound 2 |
|  |  |  |  |  | d | Compound 2 |
| Methylethyl ketone | 25 | 80 | Methanol | 7 | w | XIX |
|  |  |  |  |  | d | XIX |
| Methylethyl ketone | 17 | 80 | Ethanol | 75 | w | Compound 1 |
|  |  |  |  |  | d | Compound 1 |
| Methylethyl ketone | 17 | 80 | Water | 3 | w | XII* |
|  |  |  |  |  | d | XII* |
| Chloroform | 5 | 61 | Ether | 1 | w | Compound 1 |
|  |  |  |  |  | d | Form D |
| Chloroform | 5 | 61 | Acetone | 2 | w | Compound 2 |
|  |  |  |  |  | d | Compound 2 |
| Chloroform | 5 | 61 | Methanol | 3 | w | XIX |
|  |  |  |  |  | d | XIX |
| Chloroform | 5 | 61 | Ethanol | 16 | w | XII* |
|  |  |  |  |  | d | XII* |
| THF | 16 | 66 | Ether | 10 | w | II |
|  |  |  |  |  | d | II |
| THF | 6 | 66 | Acetone | 7 | w | II |
|  |  |  |  |  | d | II |
| THF | 7 | 66 | Methanol | 3 | w | XIX |
|  |  |  |  |  | d | XIX |
| HF | 6 | 66 | Ethanol | 21 | w | XII* |
|  |  |  |  |  | d | XII* |
| THF | 6 | 66 | 2-Propanol | 8 | w | II |
|  |  |  |  |  | d | II |
| THF | 6 | 66 | Water | 1 | w | Compound 1 |
|  |  |  |  |  | d | II |

[a]Solvent B did not form a precipitate at the reflux temperature.
[b]"Compound 1" is "crystalline Compound 1" and "Compound 2" is "crystalline Compound 2."
*Form XII may be characterized by X-ray powder diffraction peaks at 17.4, 18.2, 19.7, and 24.5 degrees two-theta, ±0.2 degrees two-theta as depicted in the XRD pattern of FIG. 7.

Example 3

Preparation of Aripiprazole Crystalline Forms by Conversion

An aripiprazole crystalline form was heated to about 100° C. to about 145° C. for about 30 to about 180 minutes until another crystalline form was formed. The resulting crystalline form was analyzed using X-ray diffraction. The results are summarized below.

TABLE 3

Conversion of Aripiprazole Crystalline forms

| Initial Crystalline Form | Heating Conditions Temp. (° C.) | Time (min) | Resulting Crystalline Form[a] |
|---|---|---|---|
| II | 130 | 180 | Form C |
| Form D | 130 | 60 | Compound 2 + VII |
| X | 100 | 60 | Compound 2 |
| XI | 100 | 60 | Compound 2 |
| XI | 130 | 60 | Compound 2 |
| XII | 100 | 60 | Compound 2 |
| XII | 130 | 60 | Compound 2 |
| Compound 1 | 135 | 30 | Form C |
| Compound | 130 | 30 | Compound 2 |
| 1 + Form D |  |  |  |
| XIX | 130 | 30 | Compound 2 |
| Compound 2 | 145 | 30 | Form C |

[a]"Compound 1" is "crystalline Compound 1" and "Compound 2" is "crystalline Compound 2."

Example 4

Preparation of Crystalline Form II by Triturating in Acetone

Aripiprazole crystalline Compound 2 (3 g) and acetone (9 mol) were added to a round bottomed flask equipped with a magnetic stirrer. The slurry was stirred at room temperature for 5 hours until a precipitate formed. The precipitate was then isolated and identified as Form II. The Form II was dried at 50° C. overnight.

Example 5

Preparation of Form XII* by Crystallization in Ethanol

Aripiprazole (30 g) and ethanol (300 ml of 95% by volume) were added to a 1 liter reactor equipped with a mechanical stirrer, forming a mixture. The mixture was heated at reflux until aripiprazole dissolved, and mechanically filtered. The resulting solution was cooled to 0° C. over a period of 6 hours, and thereafter stirred for one hour. The solution was then filtered and washed with ethanol (one volume of 95% ethanol by volume) to obtain Form XII.

Example 6

Preparation of Form XX by Drying Form XII*

Form XII (24 g) was dried in a fluidized bed dryer at 30° C. for 3.5 hours. The material was then dried at 40° C. for 1.5 hours until Form XX was obtained.

Example 7

Preparation of Crystalline Compound 2 by Drying Form XII*

Form XII (30 g) was dried in a 250 ml round-bottom 3-neck flask equipped with a mechanical stirrer at 30° C. under reduced pressure of 60 mm Hg or less. After stirring for 3 hours at 30° C., the material was stirred at 40° C. for two hours, then at 70° C. for 5 hours, and finally at 90° C. for three hours. Crystalline Compound 2 was obtained.

Example 8

Preparation of Crystalline Compound 2 by Drying Form XII*

Form XII (30 g) was dried in a 0.25 L reactor equipped with a mechanical stirrer at 30° C. under reduced pressure of 20 mm Hg or less. After stirring for 3 hours, the material was stirred at 40° C. for two hours, then at 70° C. for 5 hours, and finally at 90° C. for three hours. Crystalline compound 2 was obtained.

Example 9

Preparation of Crystalline Compound 2 by Drying Form XII*

Aripiprazole Form XII (35 g) was added to a 0.25 liter reactor equipped with a mechanical stirrer at room temperature under reduced pressure of 60 mm Hg or less. The temperature was increased gradually during 1 hour to 100° C., and maintained at 100° C. for 1 hour. Crystalline Compound 2 was obtained.

Example 10

Preparation of Crystalline Compound 2 by Drying Form XII*

Form XII (28 g) was dried in a 0.25 L reactor equipped with a mechanical stirrer at 30° C. under reduced pressure of 60 mm Hg or less. After stirring for 3 hours, the material was stirred at 40° C. for 2.5 hours, then at 70° C. for 5 hours, and finally at 90° C. for 8 hours. Crystalline Compound 2 was obtained. * Form XII may be characterized by X-ray powder diffraction peaks at 17.4, 18.2, 19.7, and 24.5 degrees two-theta, ±0.2 degrees two-theta as depicted in the XRD pattern of FIG. 7.

What is claimed is:

1. An aripiprazole crystalline Form II characterized by at least one of an XRD pattern having peaks at 16.5, 18.7, 21.9, 22.4, and 23.5 degrees two-theta, ±0.2 degrees two-theta, or a DSC scan showing a broad and small endotherm in the range of about 100° C. to about 130° C. and a melting endotherm at about 148° C. to about 150° C.; wherein said crystal form contains less than 40% by weight of other aripiprazole crystal forms.

2. The aripiprazole crystalline form of claim 1, further characterized by XRD peaks at 10.2, 11.8, 20.0, 20.7, 26.2, 27.3, and 29.0 degrees two-theta, ±0.2 degrees two-theta.

3. The aripiprazole crystalline form of claim 1, having less than 40% by weight of aripiprazole crystalline compound 1, crystalline compound 2, crystalline form C, or crystalline form D.

4. The aripiprazole crystalline form of claim 3, having less than 30% by weight of aripiprazole crystalline compound 1, crystalline compound 2, crystalline form C, or crystalline form D.

5. The aripiprazole crystalline form of claim 4, having less than 20% by weight of aripiprazole crystalline compound 1, crystalline compound 2, crystalline form C, or crystalline form D.

6. The aripiprazole crystalline form of claim 5, having less than 10% by weight of aripiprazole crystalline compound 1, crystalline compound 2, crystalline form C, or crystalline form D.

7. The aripiprazole crystalline form of claim 6, having less than 5% by weight of aripiprazole crystalline compound 1, crystalline compound 2, crystalline form C, or crystalline form D.

8. The aripiprazole crystalline form of claim 1, having between 5% and 40% by weight of aripiprazole crystalline compound 1, crystalline compound 2, crystalline form C, or crystalline form D.

9. The aripiprazole crystalline form of claim 1, having between 5% and 30% by weight of aripiprazole crystalline compound 1, crystalline compound 2, crystalline form C, or crystalline form D.

10. The aripiprazole crystalline form of claim 1, having between 5% and 20% by weight of aripiprazole crystalline compound 1, crystalline compound 2, crystalline form C, or crystalline form D.

11. The aripiprazole crystalline form of claim 1, having between 5% and 10% by weight of aripiprazole crystalline compound 1, crystalline compound 2, crystalline form C, or crystalline form D.

* * * * *